(12) United States Patent
Hoe et al.

(10) Patent No.: US 11,826,368 B2
(45) Date of Patent: Nov. 28, 2023

(54) PHARMACEUTICAL COMPOSITION COMPRISING IBRUTINIB AS EFFECTIVE INGREDIENT FOR PREVENTING OR TREATING DEGENERATIVE BRAIN DISEASE

(71) Applicant: DAEGU GYEONGBUK INSTITUTE OF SCIENCE AND TECHNOLOGY, Dalseong-gun Daegu (KR)

(72) Inventors: Hyang Sook Hoe, Dong-gu Daegu (KR); Jeoung Yeon Kim, Seodaemun-gu Seoul (KR); Hye Yeon Nam, Suseong-gu Daegu (KR); Ju Young Lee, Dalseo-gu Daegu (KR); Young Pyo Nam, Buk-gu Daegu (KR); Ri Jin Kang, Gwangjin-gu Seoul (KR); Hyun Ju Lee, Dalseong-gun Daegu (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 285 days.

(21) Appl. No.: 17/050,800

(22) PCT Filed: Apr. 26, 2019

(86) PCT No.: PCT/KR2019/005063
§ 371 (c)(1),
(2) Date: Jan. 11, 2021

(87) PCT Pub. No.: WO2019/209065
PCT Pub. Date: Oct. 31, 2019

(65) Prior Publication Data
US 2021/0322419 A1    Oct. 21, 2021

(30) Foreign Application Priority Data

Apr. 27, 2018  (KR) .................. 10-2018-0049429
Apr. 25, 2019  (KR) .................. 10-2019-0048689

(51) Int. Cl.
*A61K 31/519*   (2006.01)
*A61P 25/28*    (2006.01)

(52) U.S. Cl.
CPC ............ *A61K 31/519* (2013.01); *A61P 25/28* (2018.01)

(58) Field of Classification Search
CPC ........ A61K 31/519; A61P 25/28; A61P 25/16; A61P 25/00
See application file for complete search history.

(56) References Cited

U.S. PATENT DOCUMENTS

| 7,514,444 | B2  |         | 4/2009 | Honigberg et al. |
|---|---|---|---|---|
| 2015/0104467 | A1 | * | 4/2015 | Constantin .............. A61P 25/28 530/388.7 |
| 2017/0119760 | A1 |   | 5/2017 | Moussy et al. |

FOREIGN PATENT DOCUMENTS

| KR | 1020150032340 A | 3/2015 |
|---|---|---|
| WO | 2017/077507 A1 | 5/2017 |
| WO | 2017212420 A1 | 12/2017 |

OTHER PUBLICATIONS

Bischoff et al., Definition of leukocyte subsets in primate central nervous system by polychromatic flow cytometry, Cytometry Part A, Journal of the International Society for Advancement of Cytometry, vol. 79A, 436-445, 2011 (Year: 2011).*

(Continued)

*Primary Examiner* — Kortney L. Klinkel
*Assistant Examiner* — Padmaja S Rao
(74) *Attorney, Agent, or Firm* — Sughrue Mion, PLLC

(57) ABSTRACT

The present disclosure relates to a pharmaceutical composition comprising ibrutinib as an effective ingredient for (Continued)

preventing or treating neurodegenerative brain disease. Ibrutinib according to the present disclosure inhibits LPS-induced proinflammatory cytokine levels and BV2 microglial cell migration. In addition, ibrutinib treatment significantly reduced LPS-mediated microglial and astroglial activation. Ibrutinib treatment significantly diminished AP plaque numbers, tau hyperphosphorylation, and tau kinase CDK5 phosphorylation. Moreover, ibrutinib treatment enhances memory and thus can be used as a therapeutic agent for prevention or treatment of neurodegenerative brain disease.

13 Claims, 24 Drawing Sheets

(56) References Cited

OTHER PUBLICATIONS

English Translation of International Search Report for PCT Application No. PCT/KR2019/005063, dated Aug. 1, 2020, pp. 1-2.
Ito et al., "Bruton's tyrosine kinase is essential for NLRP3 inflammasome activation and contributes to ischaemic brain injury," Nature Communications, vol. 6, Article No. 7360, pp. 1-11, 2015.
Wei et al., "Preclinical investigation of ibrutinib, a Bruton's kinase tyrosine (Btk) inhibitor, in suppressing glioma tumorigenesis and stem cell phenotypes," Oncotarget, vol. 7, No. 43, p. 69961-69975, Aug. 24, 2016.
Office Action in Japanese Patent Application No. 2020-560335 dated Nov. 18, 2021.
Extended European Search Report in European Application No. 19793308.8 dated Nov. 30, 2021.
Ito et al., "Bruton's tyrosine kinase is essential for NLRP3 inflammasome activation and contributes to ischaemic brain Injury", Nature Communications DOI: 10.1038/ncomms8360, vol. 6, Jun. 10, 2015, 11 pages.
Lee et al., "Ibrutinib modulates A[beta]/tau pathology, neuroinflammation, and cognitive function in mouse models of Alzheimer's disease", Aging Cell, vol. 20, No. 3, Mar. 11, 2021, 16 pages.
Nam et al., "Ibrutinib suppresses LPS-induced neuroinflammatory responses in BV2 microglial cells and wild-type mice," Journal of Neuroinflammation, vol. 15, No. 271, Sep. 19, 2018, 22 pages.
Wei et al., "Preclinical investigation of ibrutinib, a Bruton's kinase tyrosine (Btk) inhibitor, in suppressing glioma tumorigenesis and stem cell phenotypes," Oncotarget, vol. 7, No. 43, Aug. 24, 2016, 13 pages.

* cited by examiner

[fig. 1]
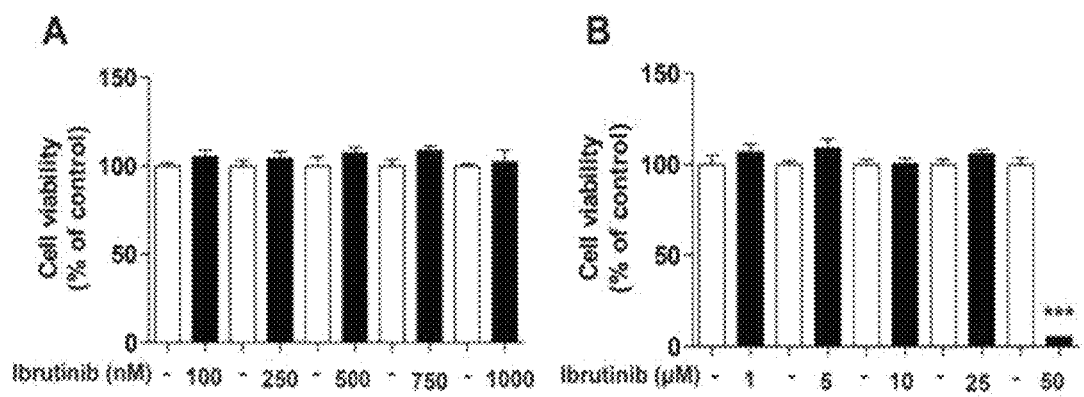
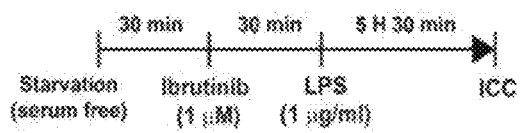
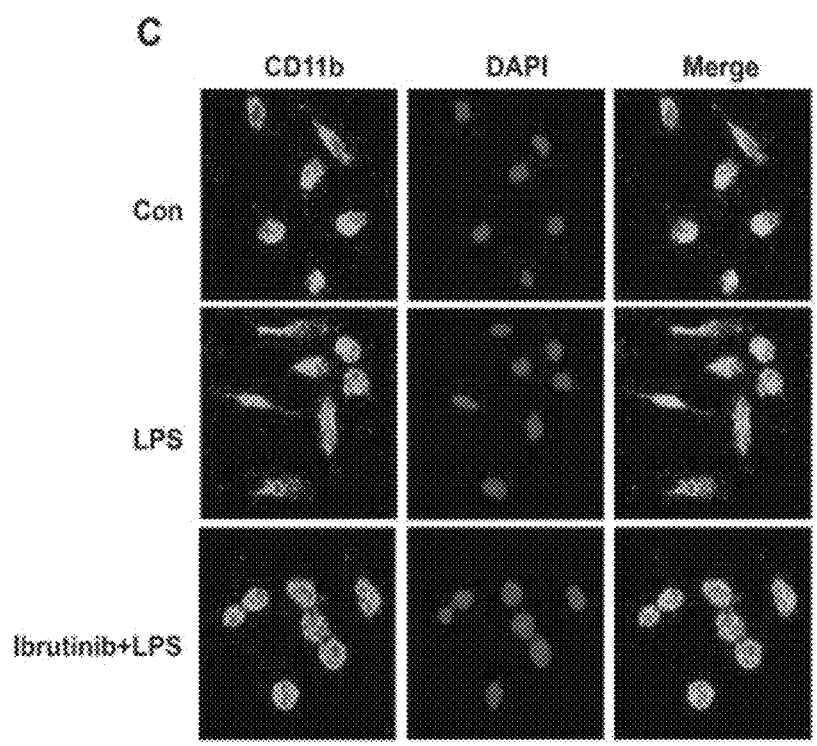

[fig. 2]
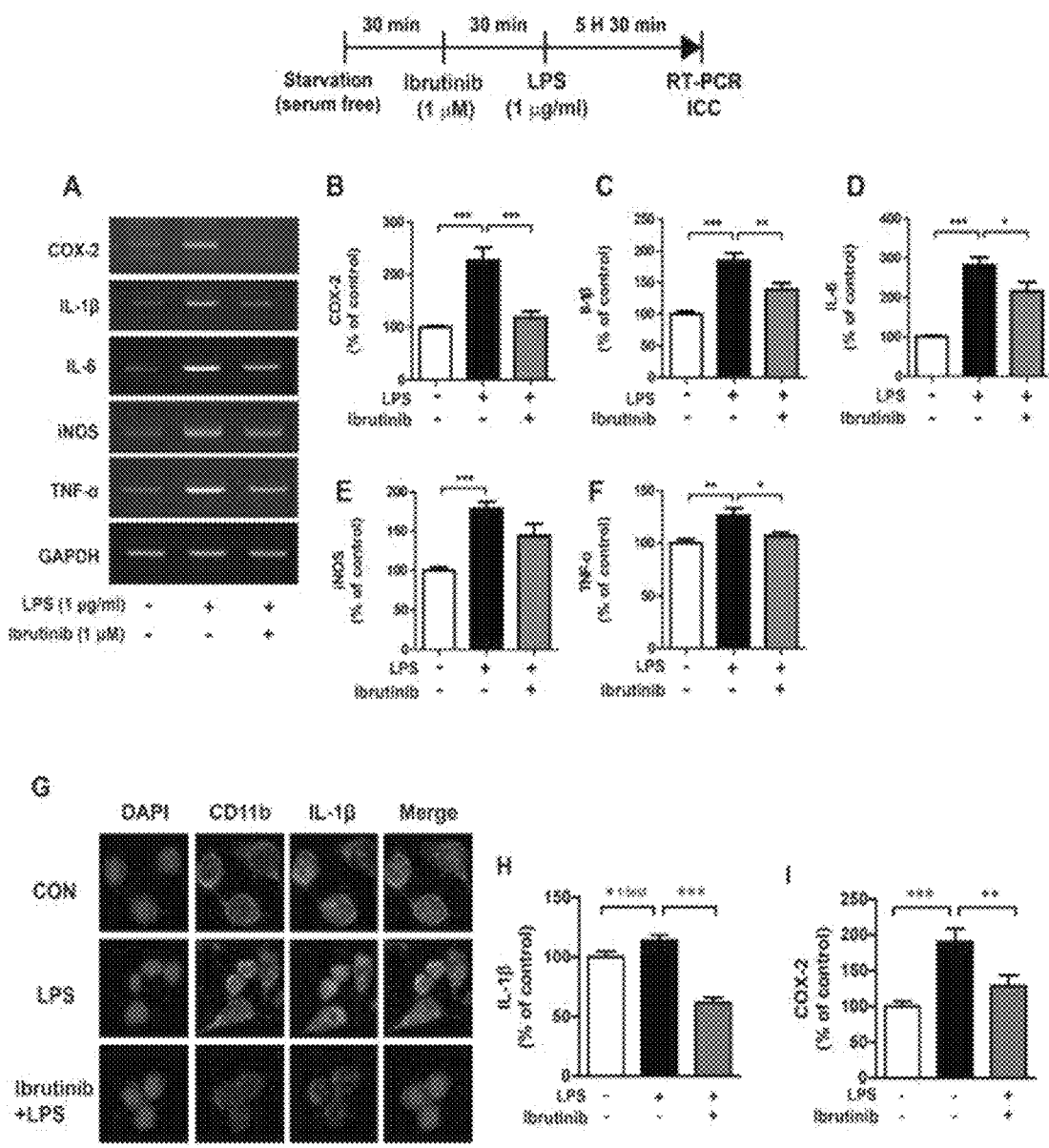

[fig. 3]
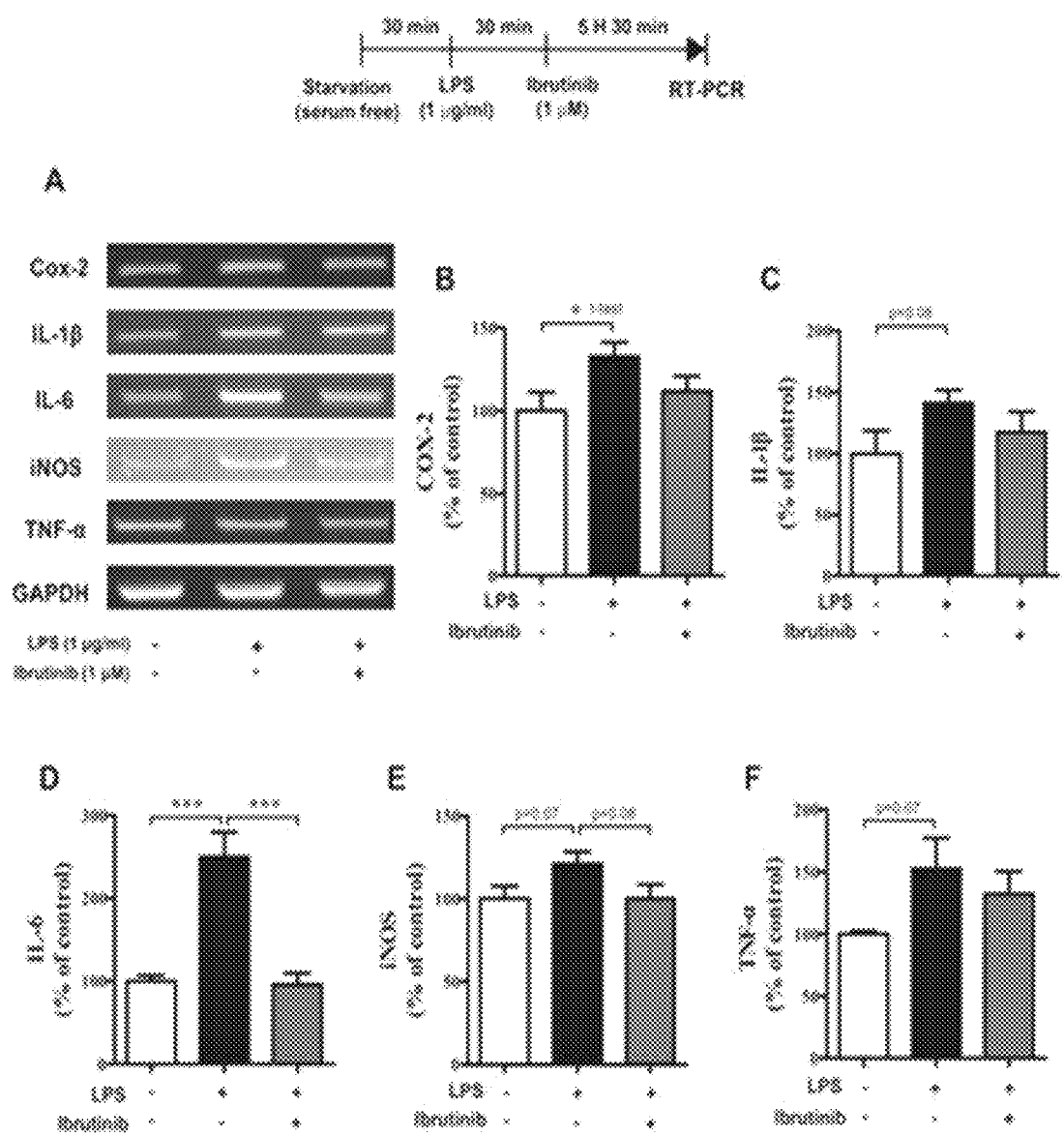

[fig. 4]
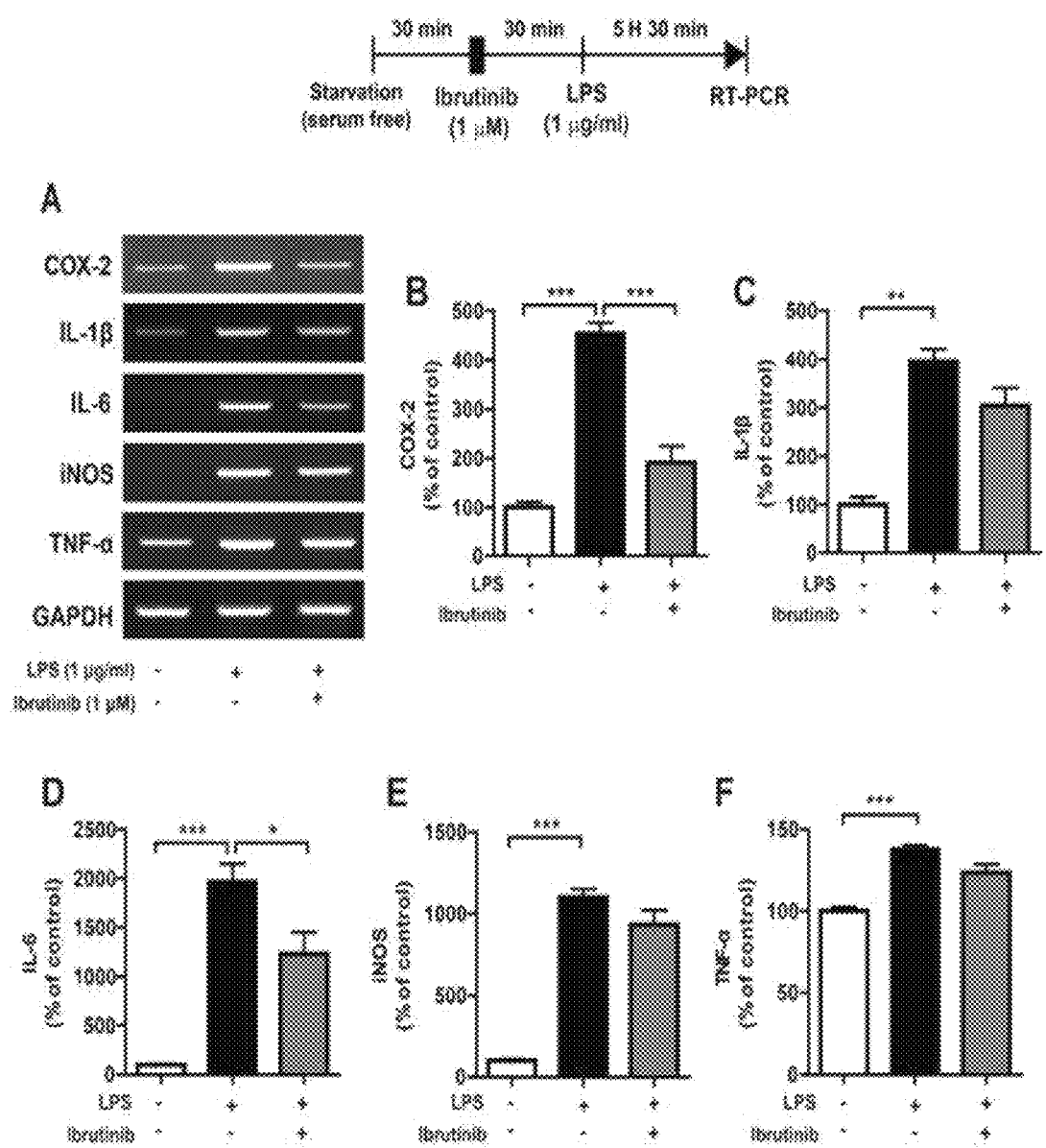

[fig. 5]
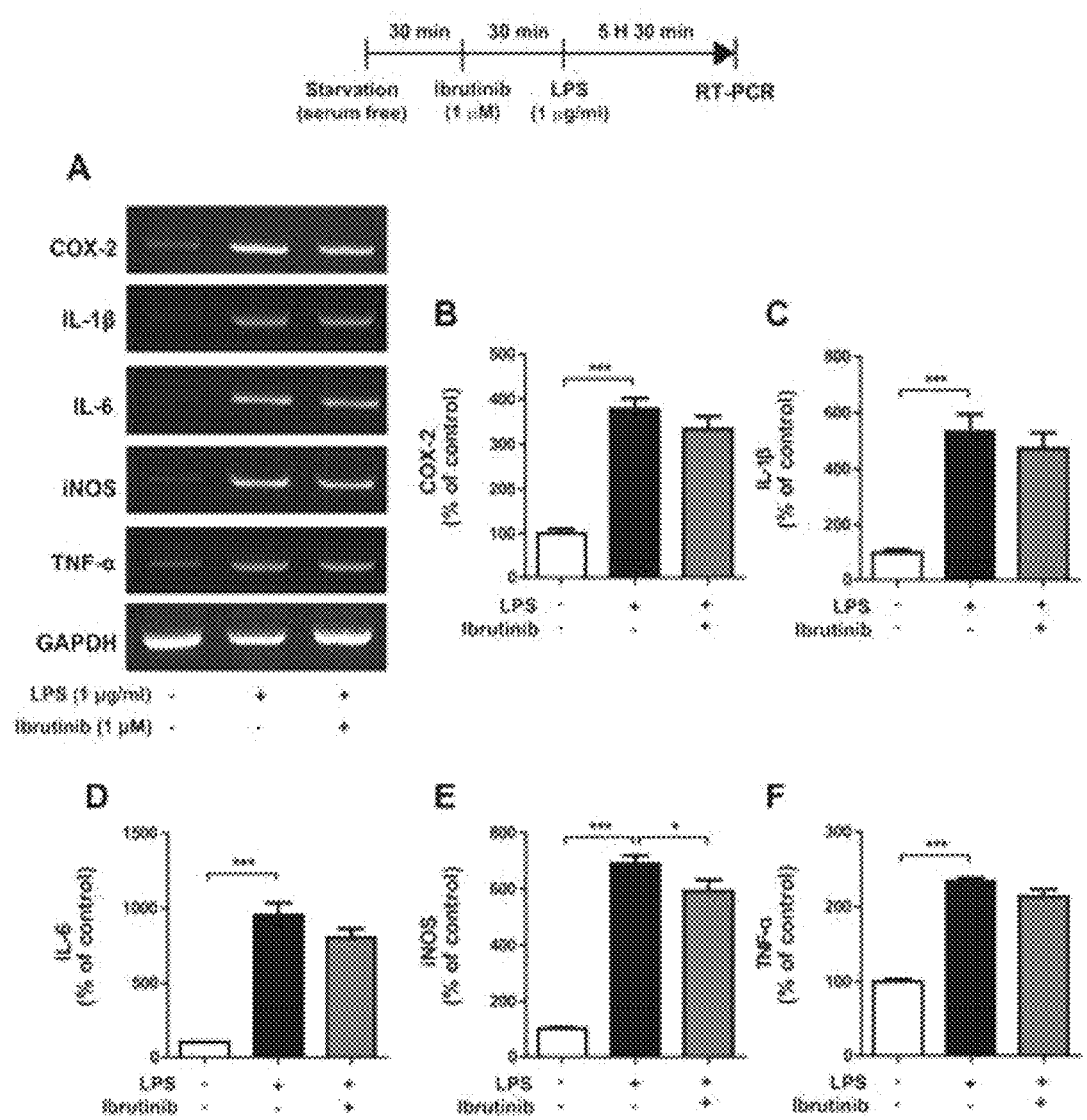

[fig. 6]
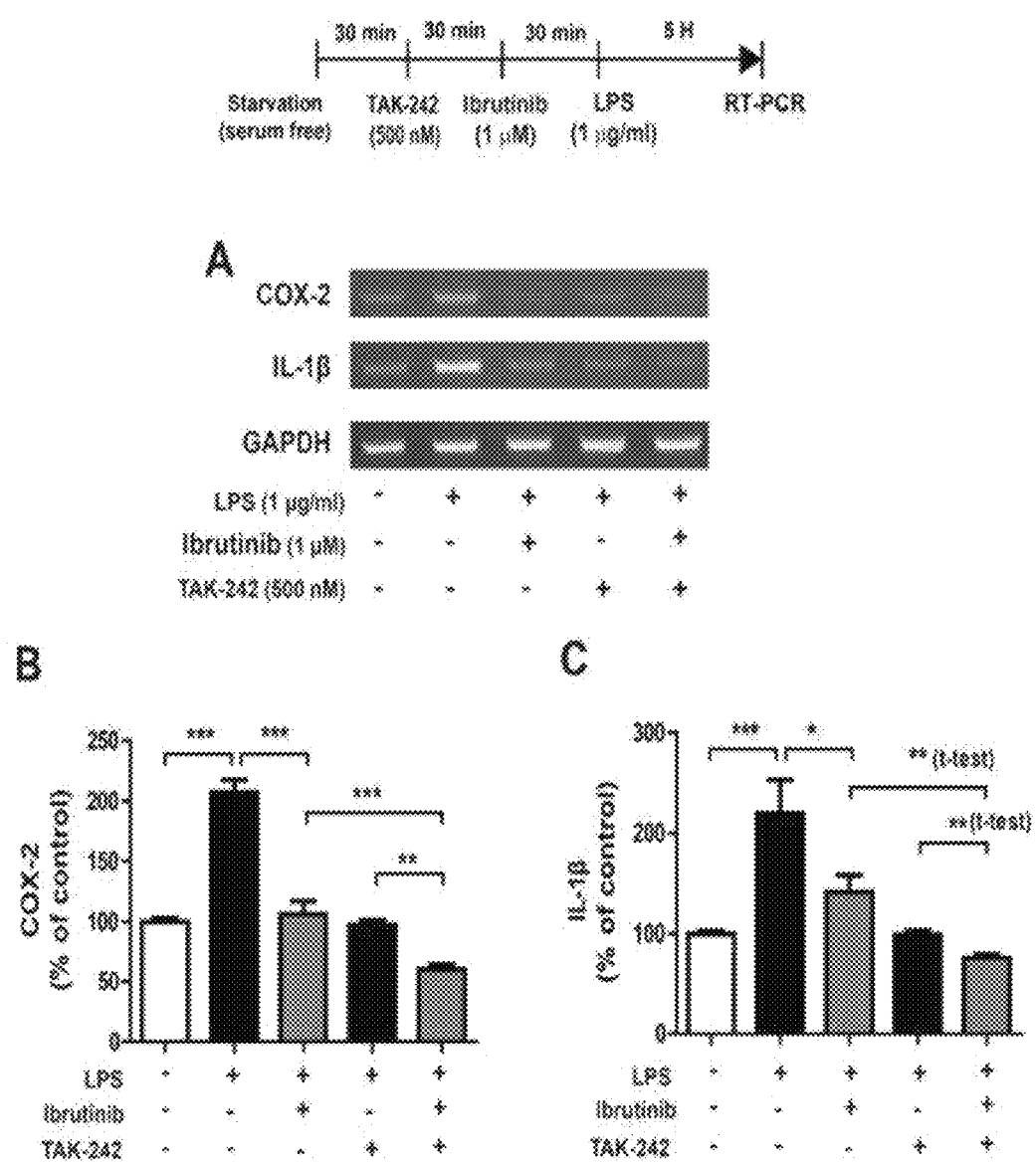

[fig. 7]
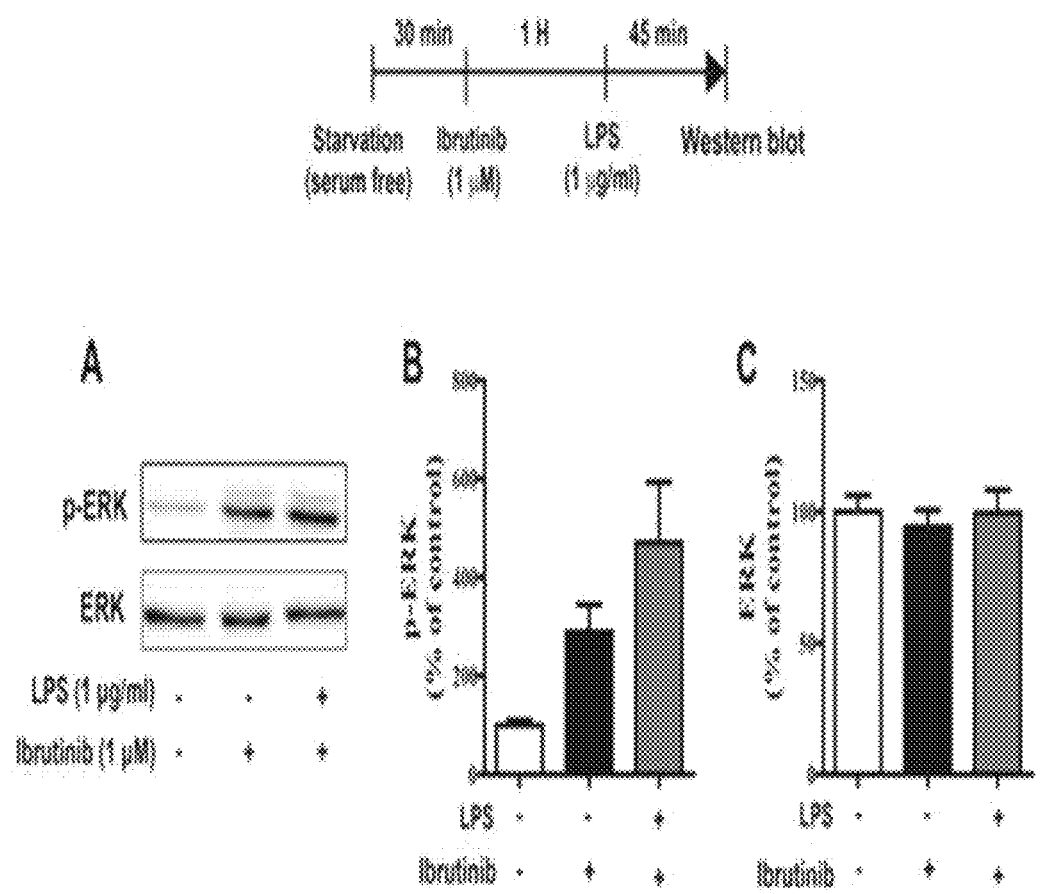

[fig. 8]
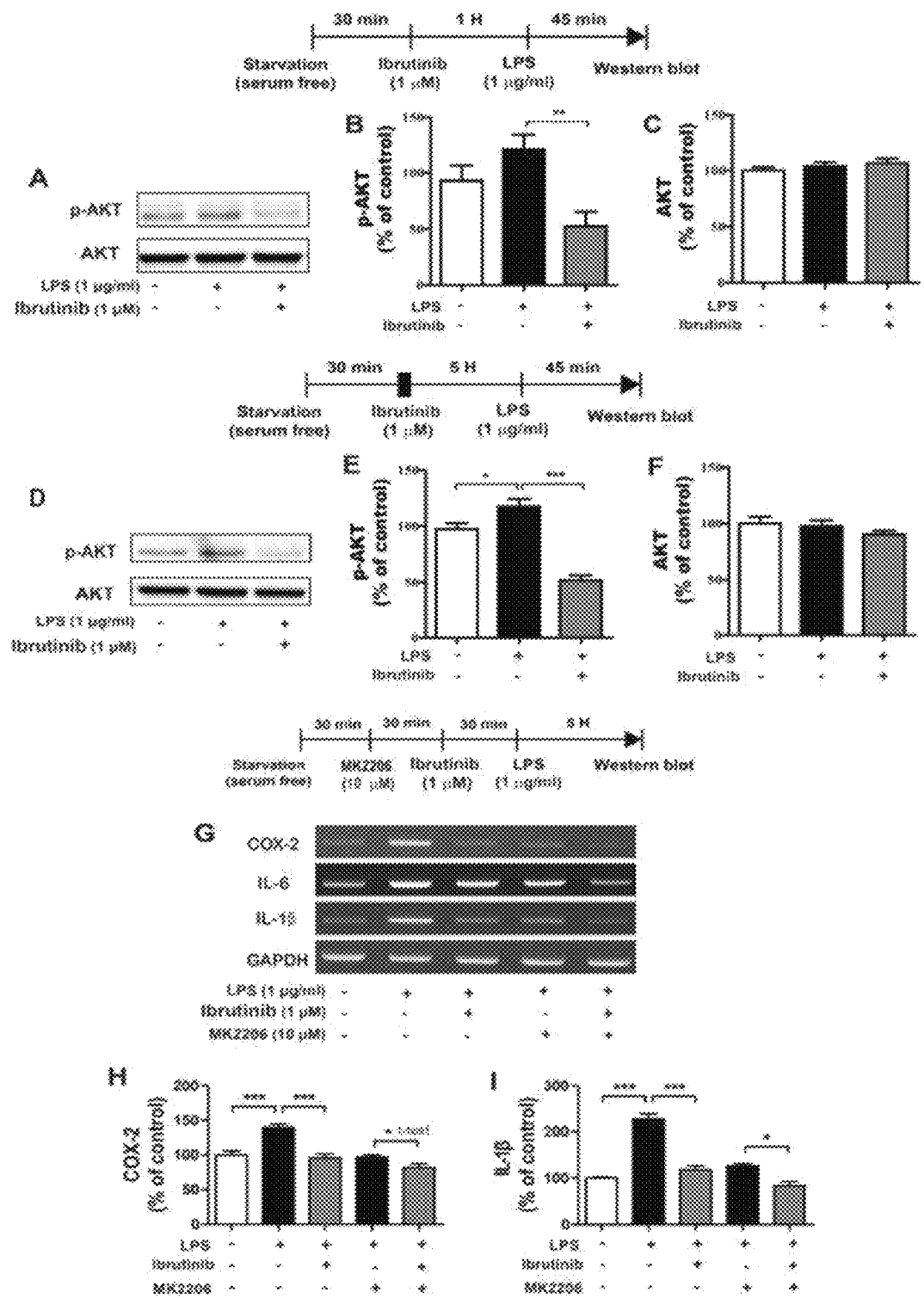

[fig. 9]
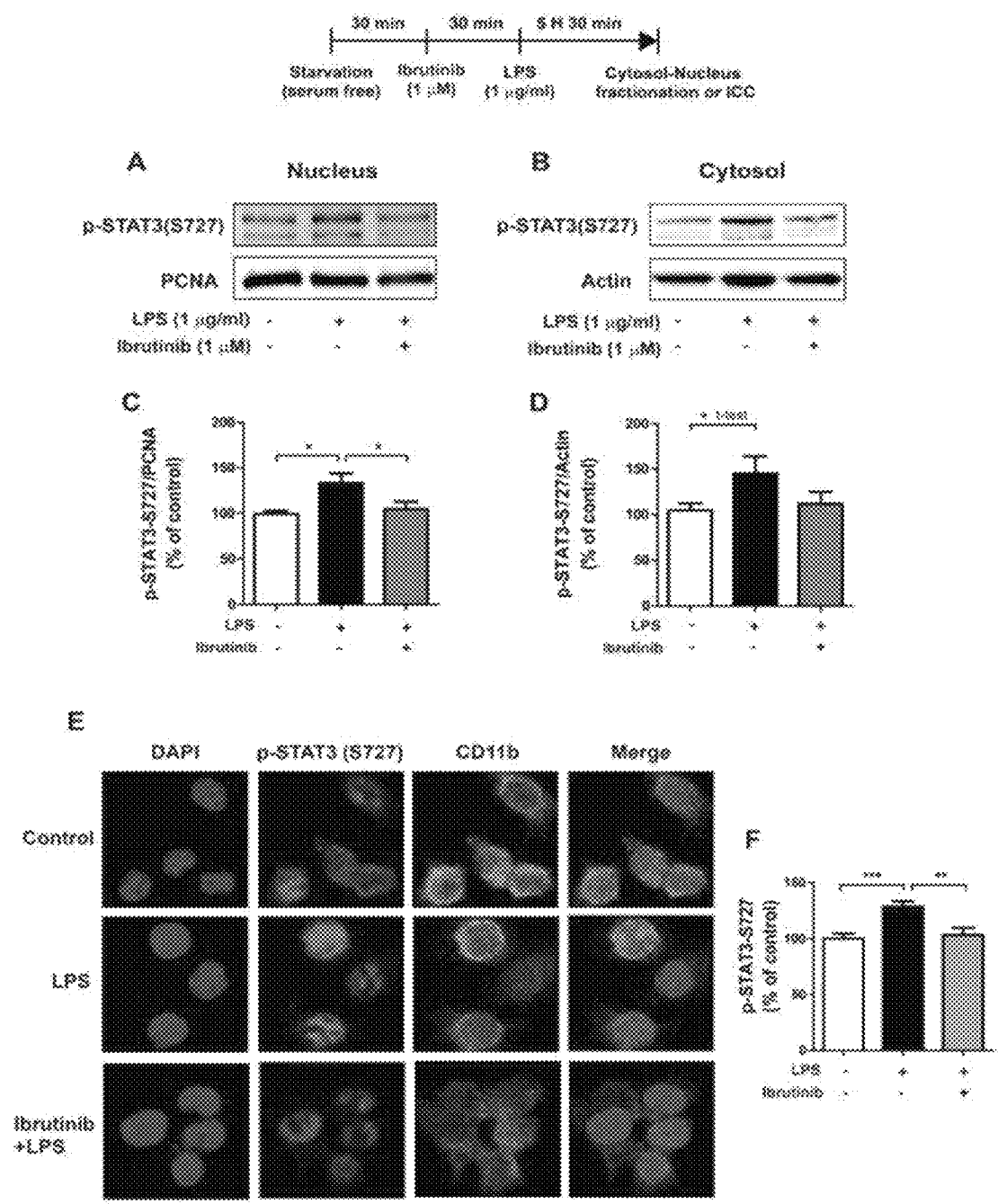

[fig. 10]
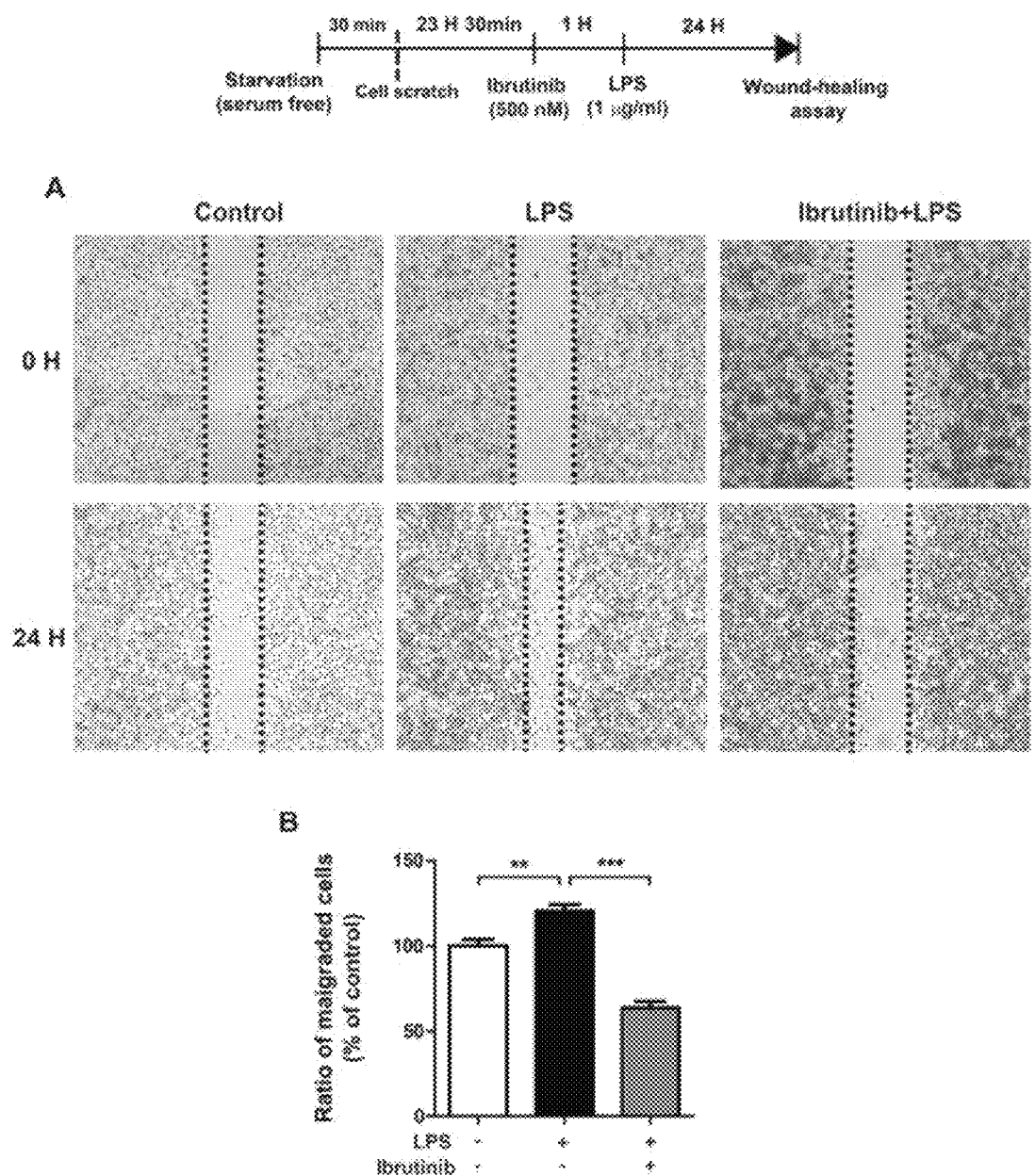

[fig. 11]
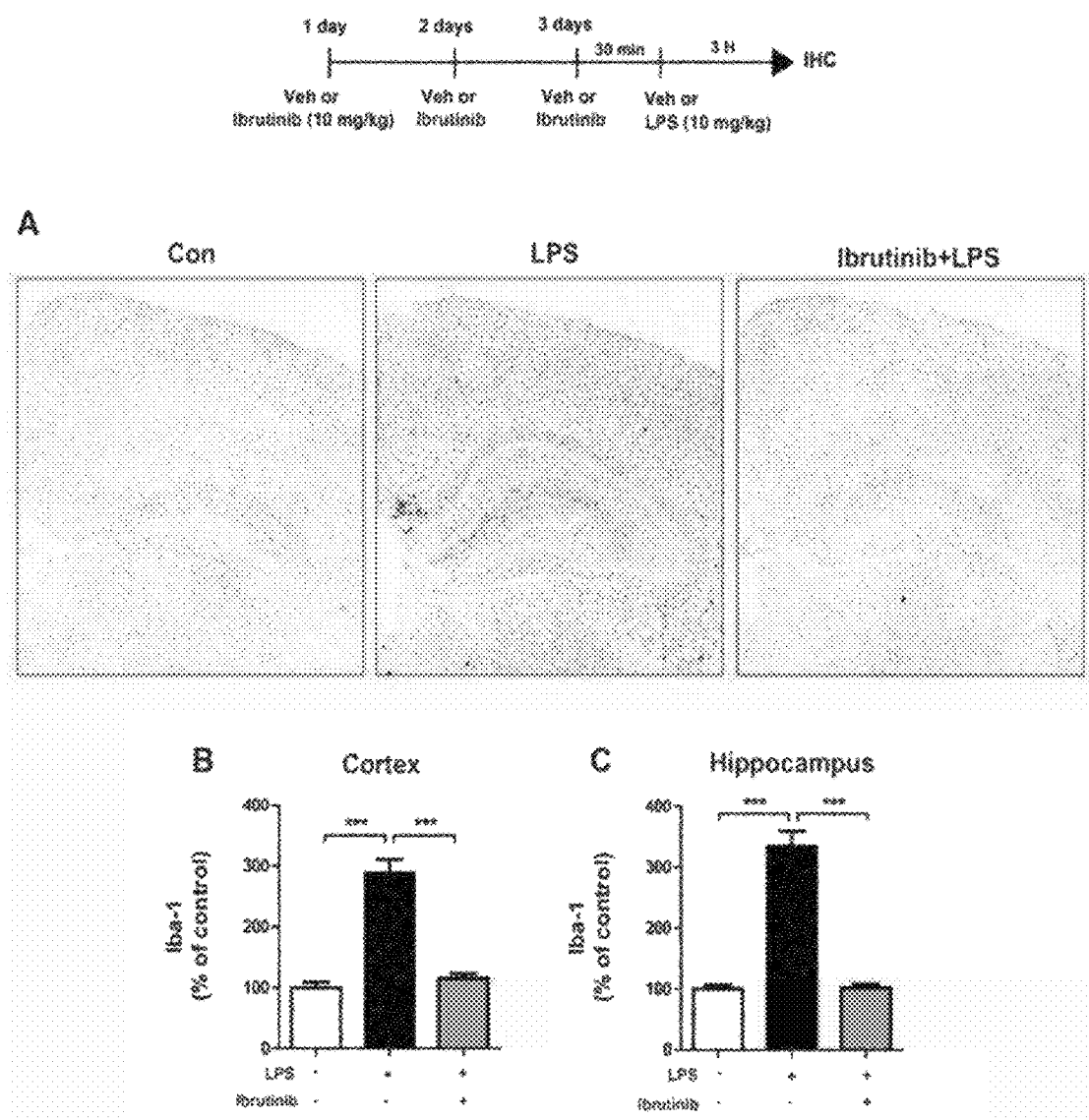

[fig. 12]
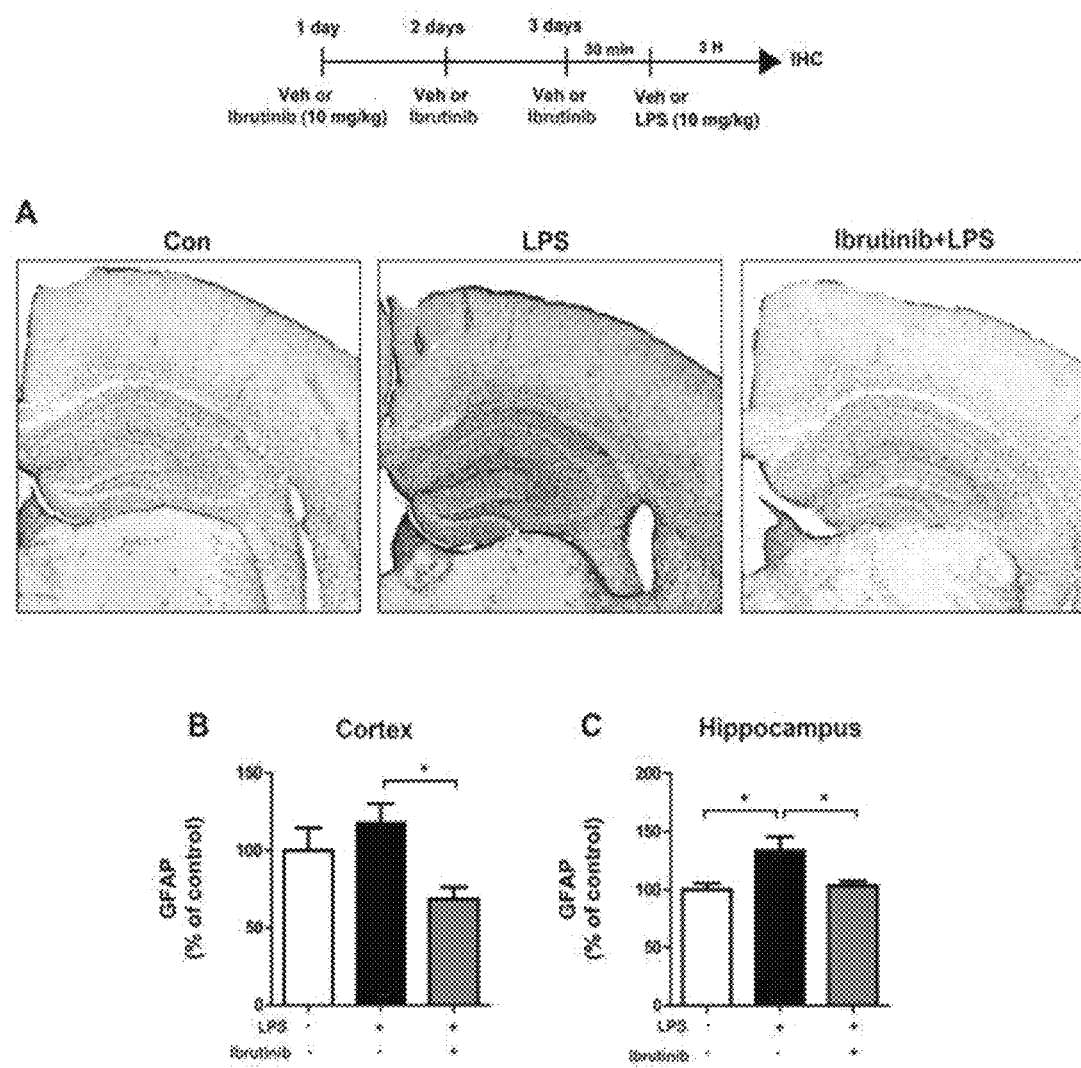

[fig. 13]
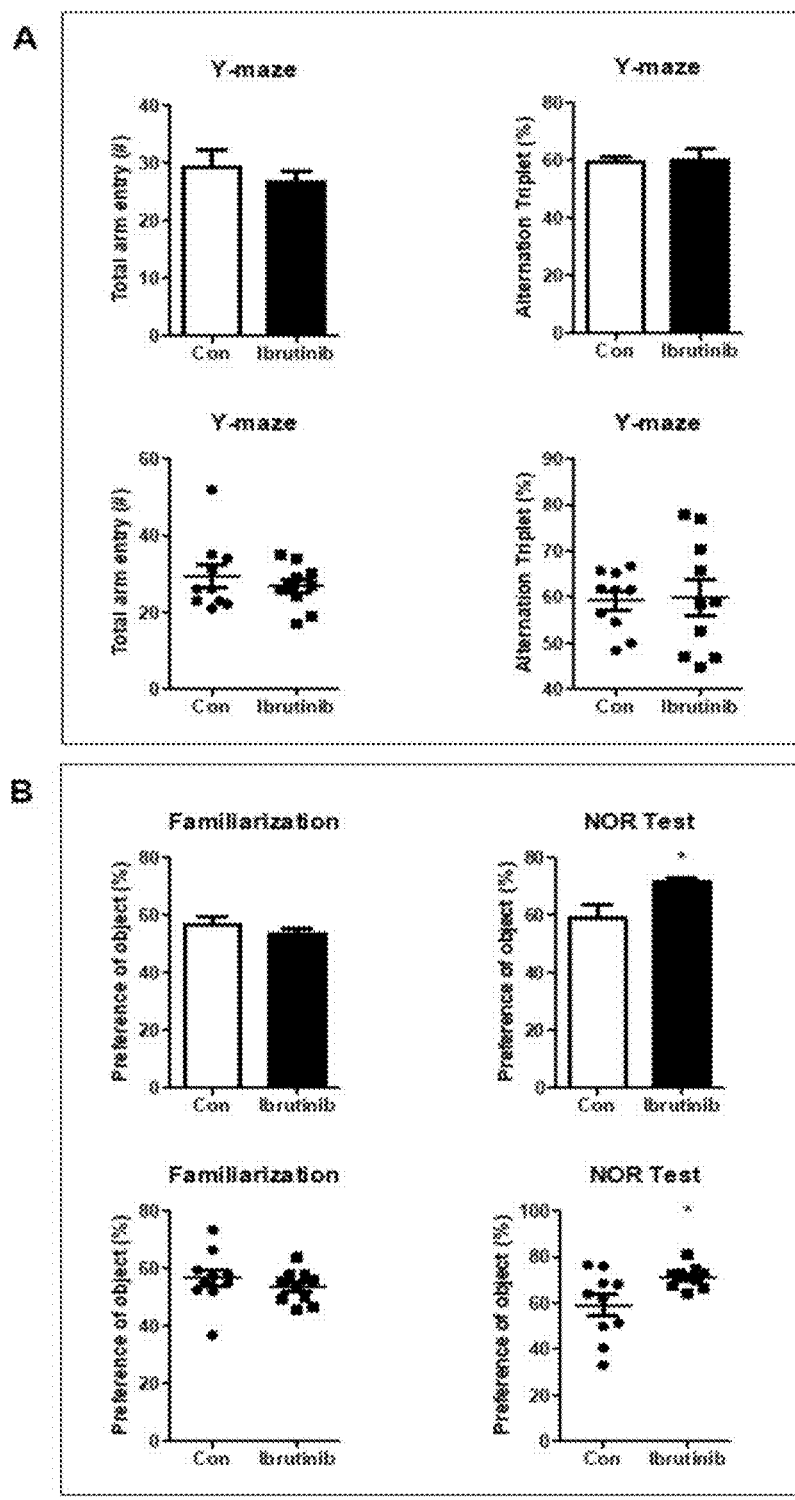

[fig. 14]
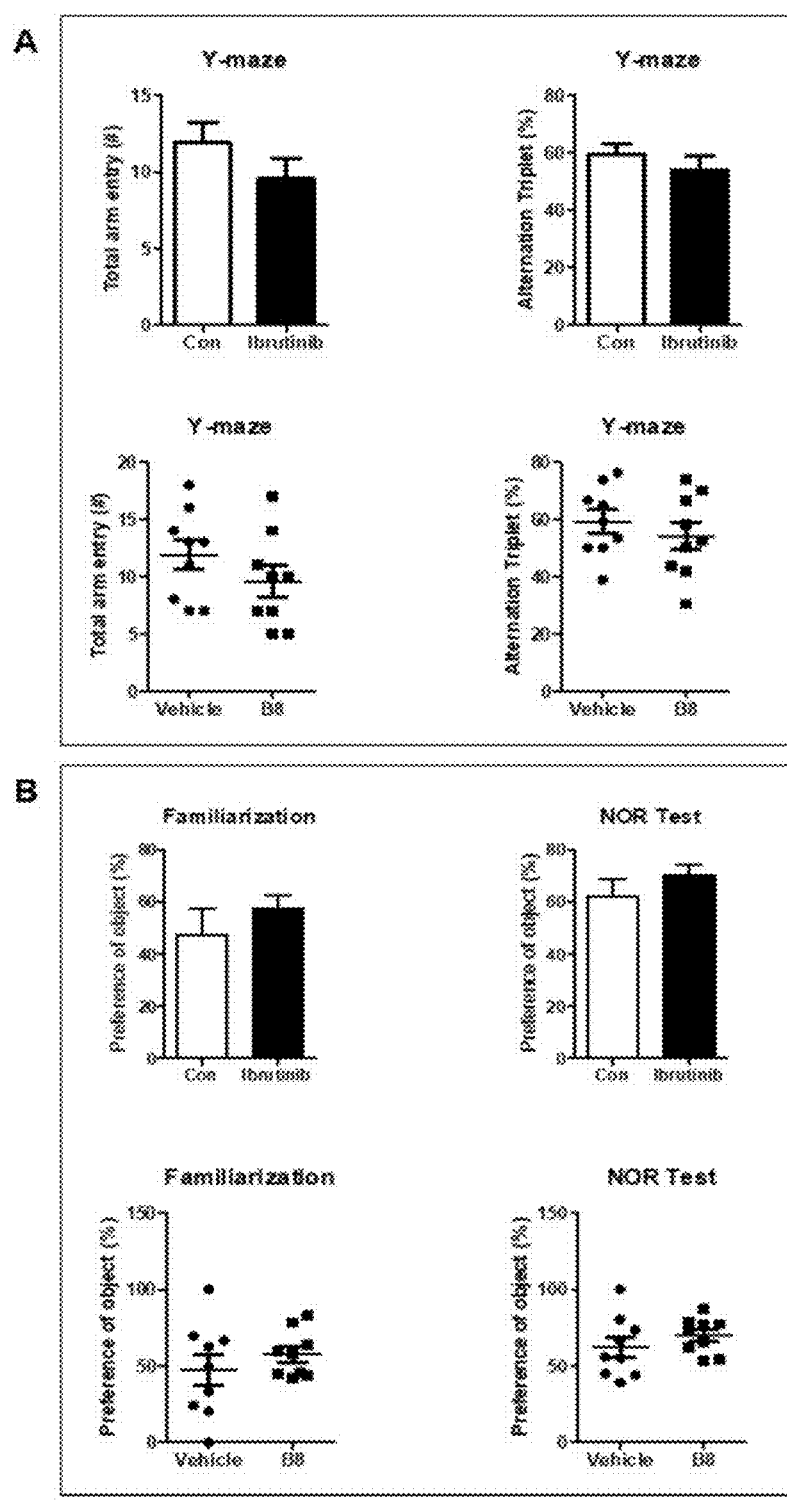

[fig. 15]
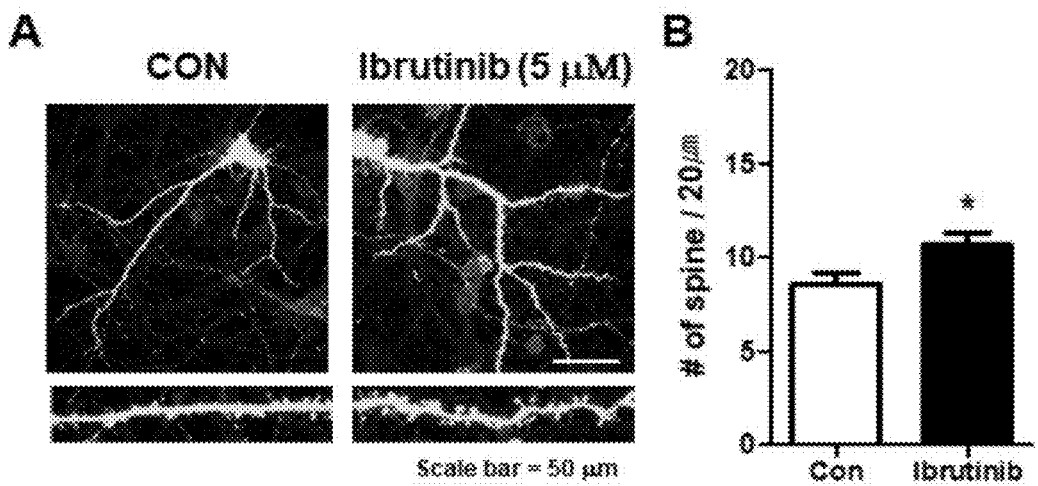
[fig. 16]
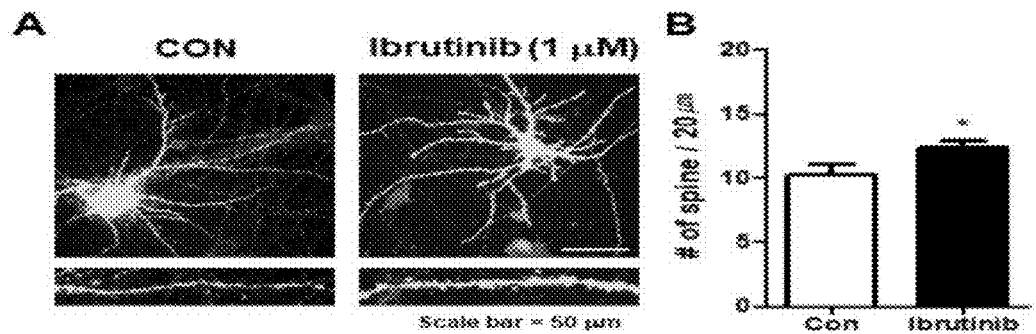
[fig. 17]
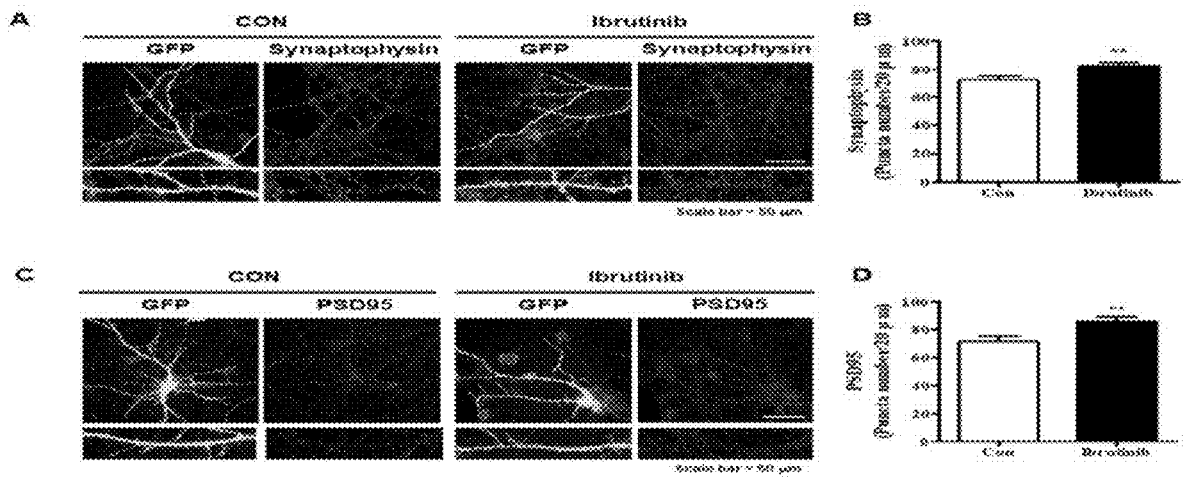

[fig. 18]
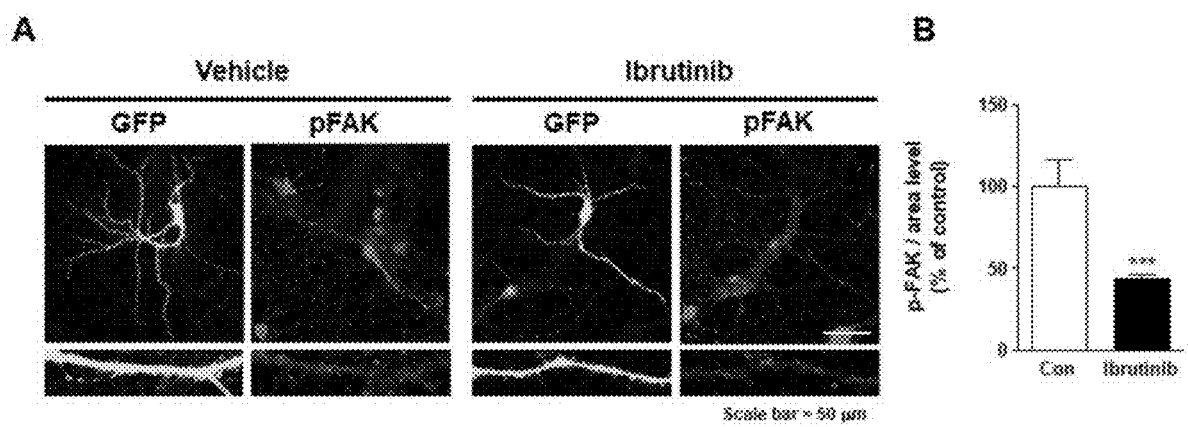
[fig. 19]
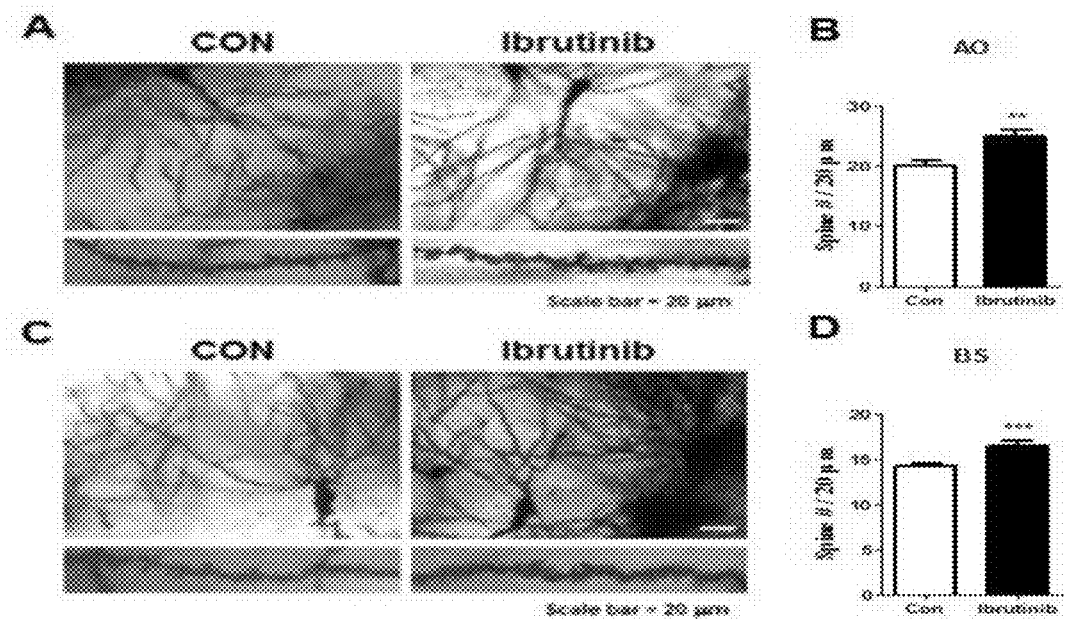

[fig. 20]
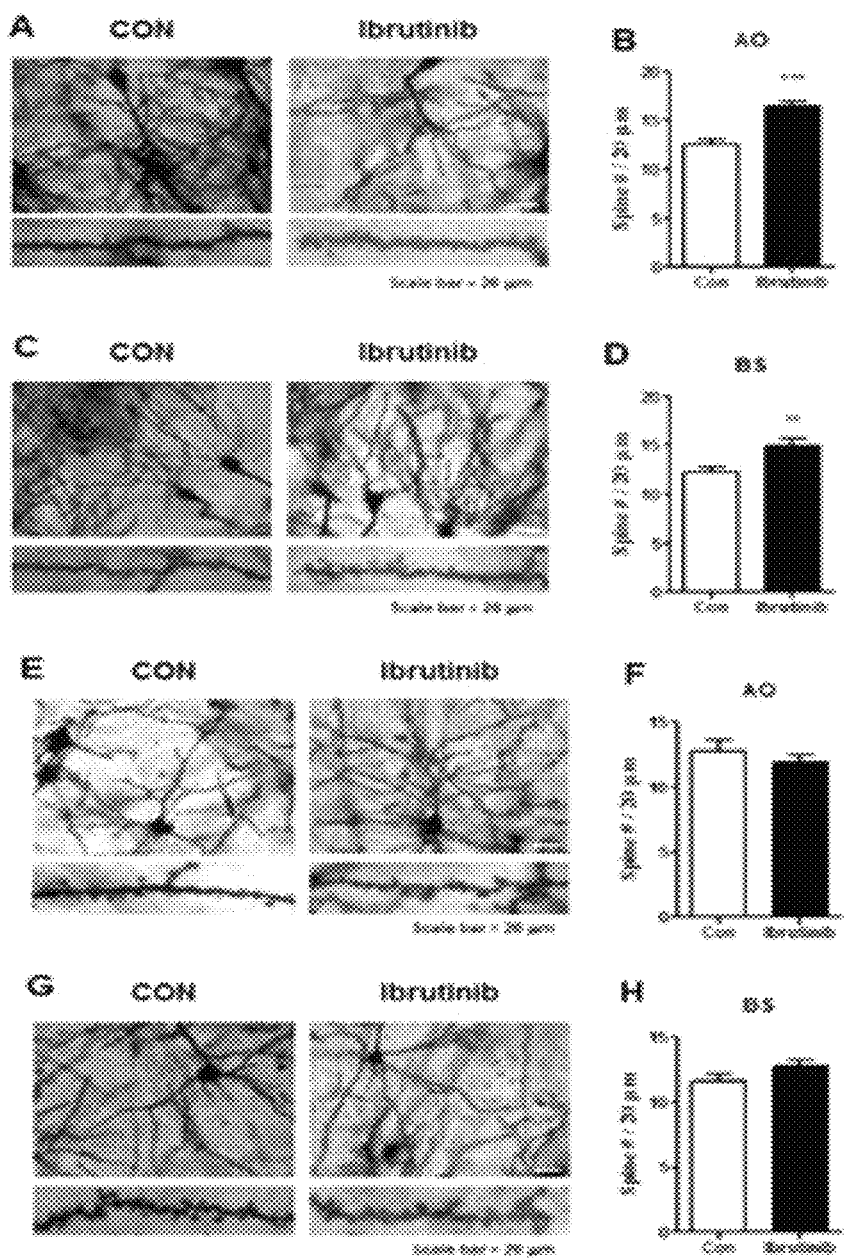

[fig. 21]
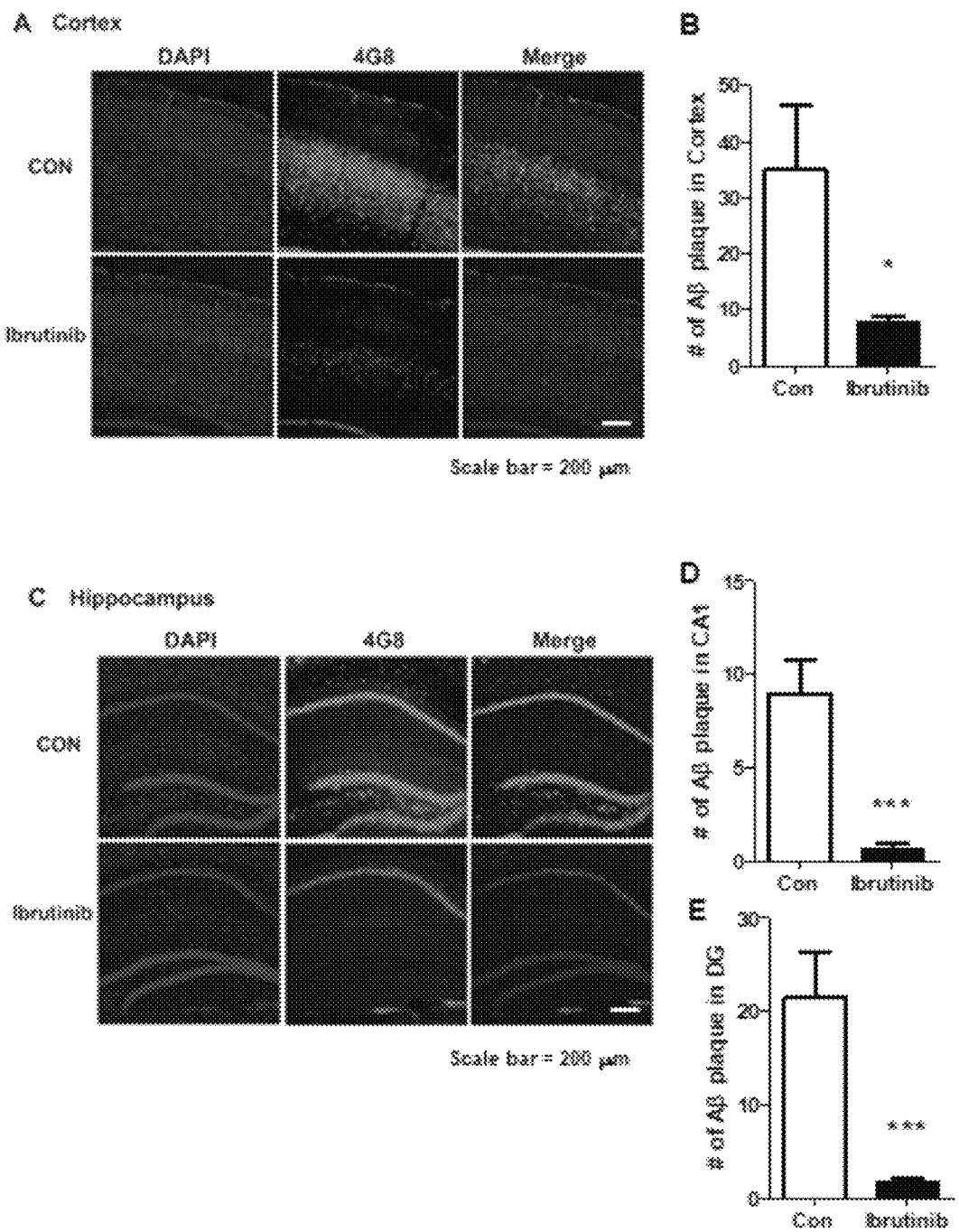

[fig. 22]
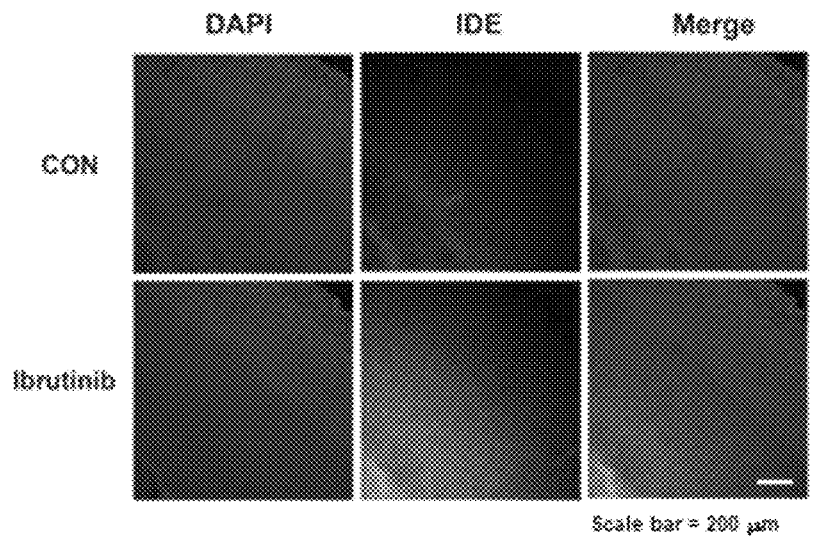
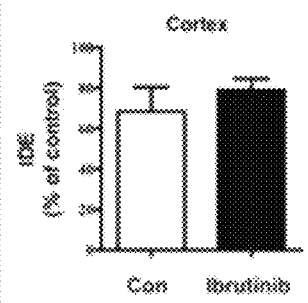
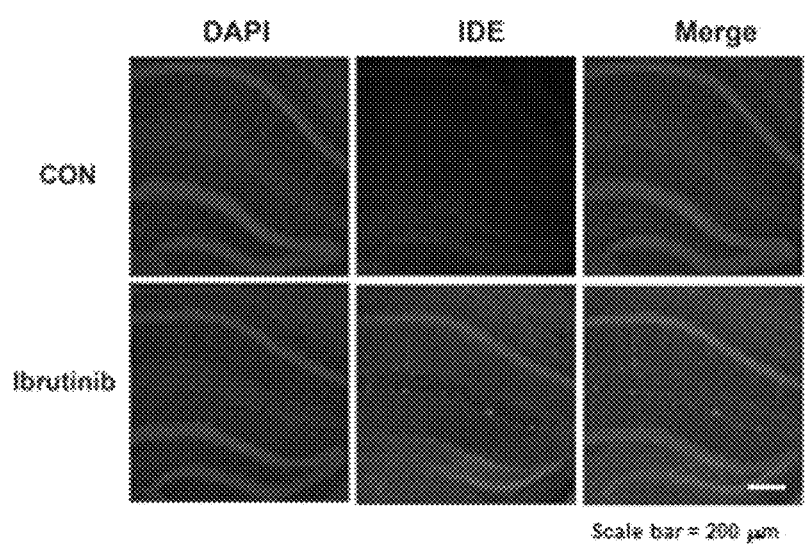
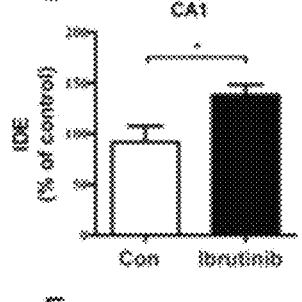
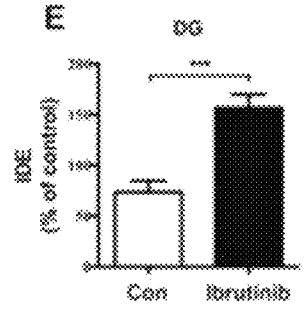

[fig. 23]
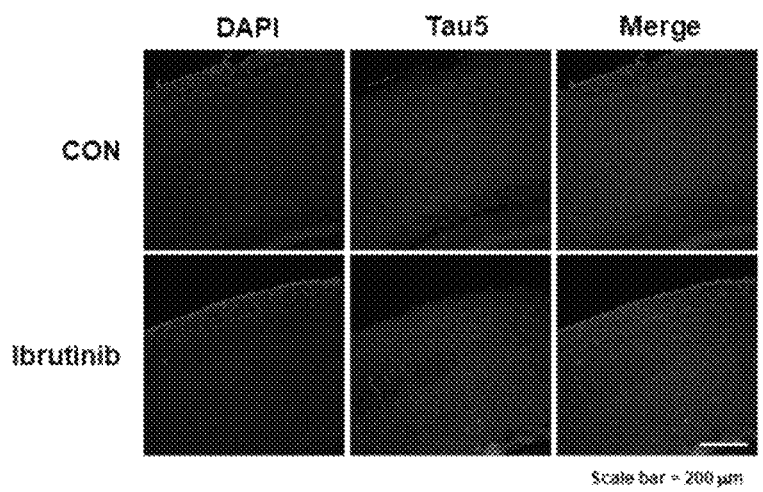
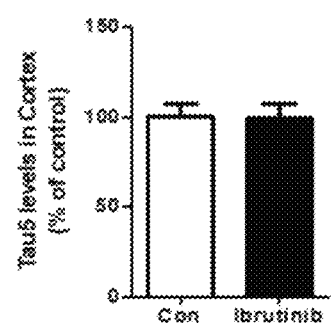
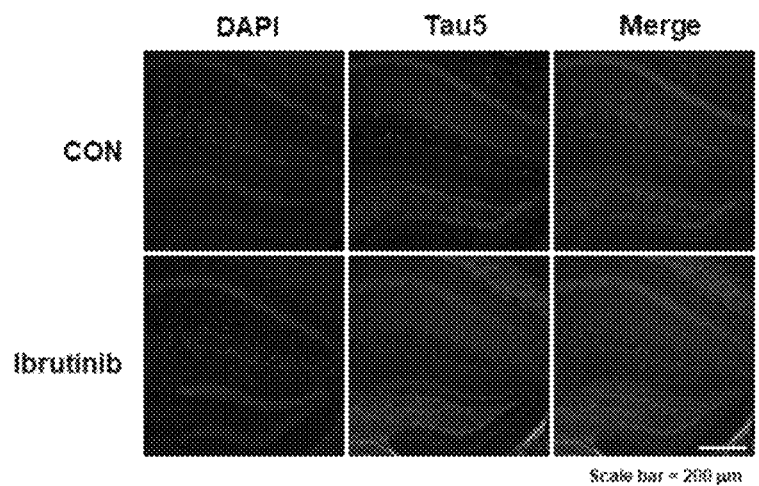
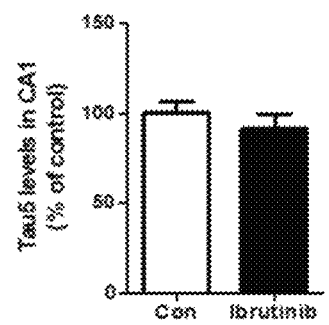
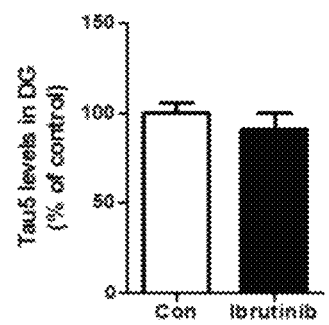

[fig. 24]
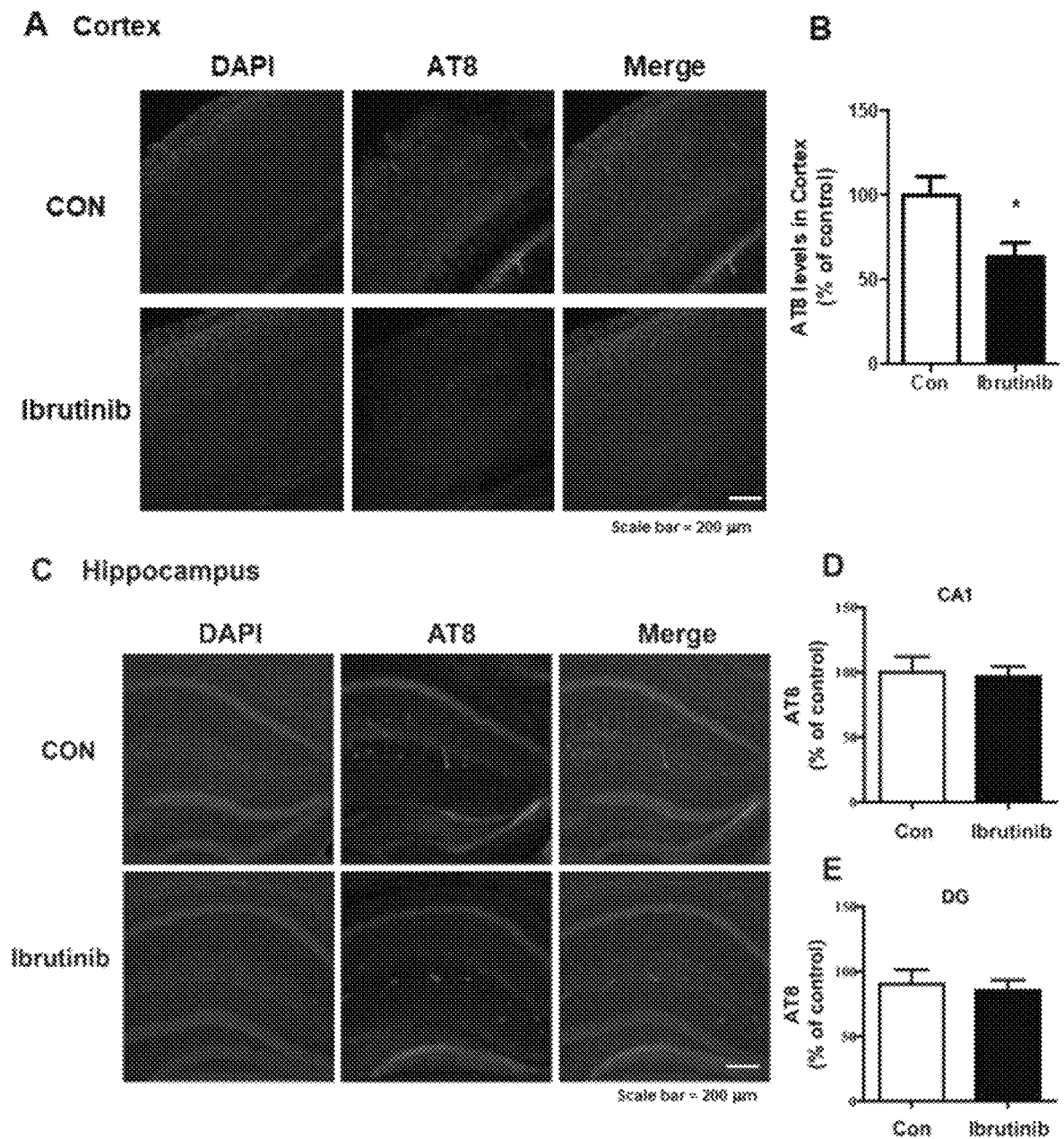

[fig. 25]
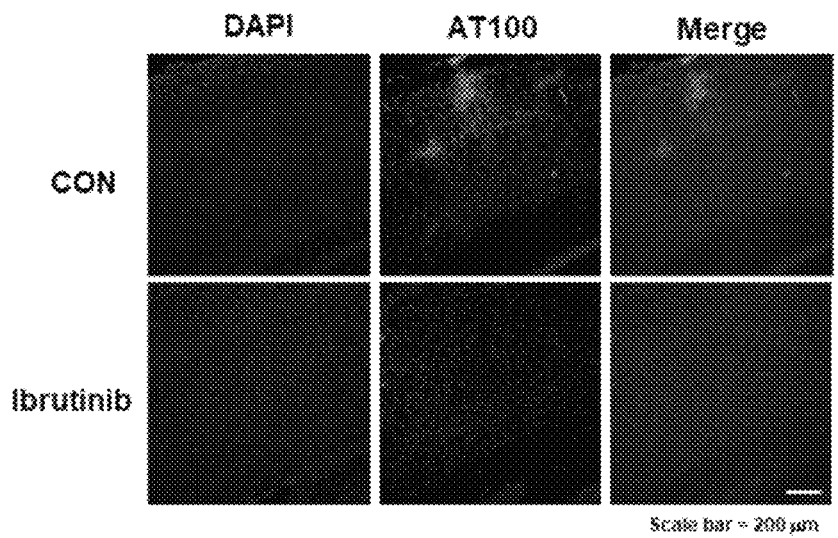
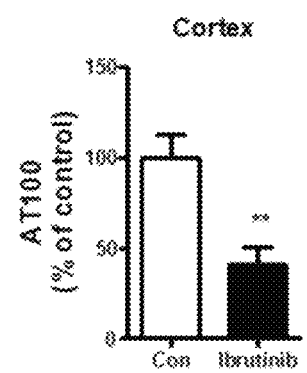
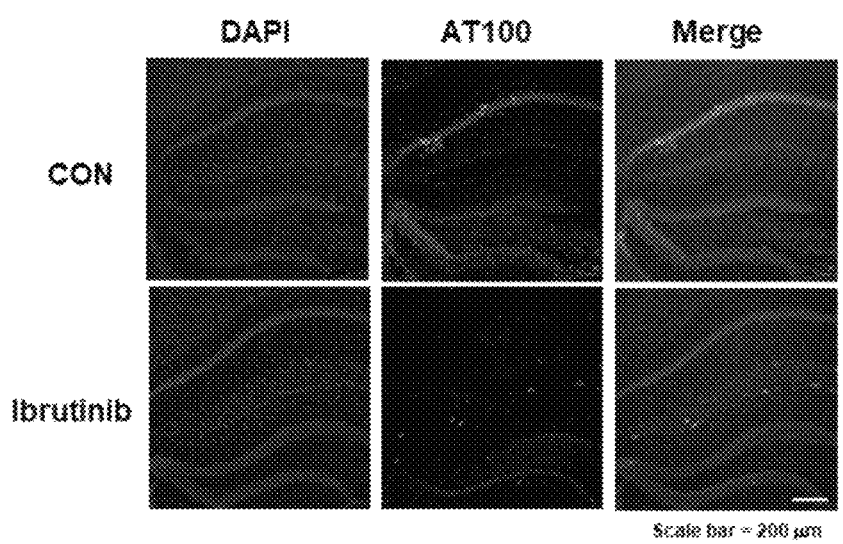
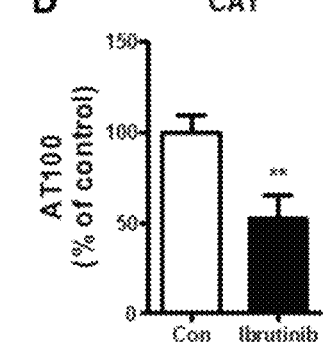
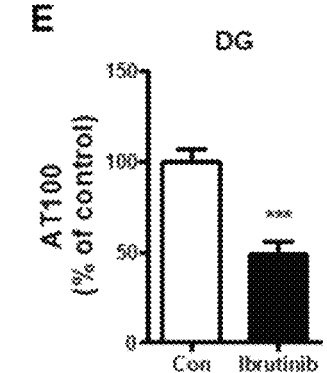

[fig. 26]
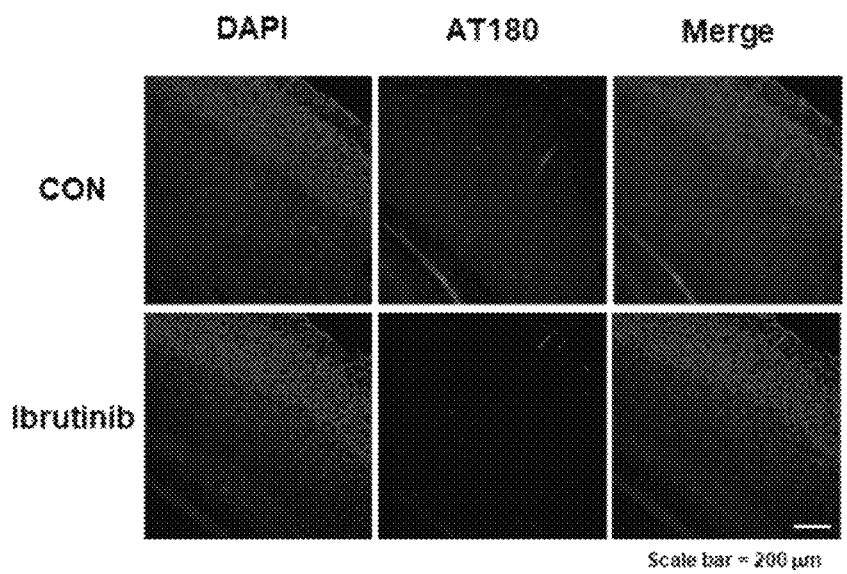
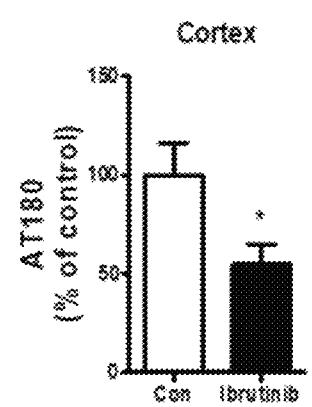
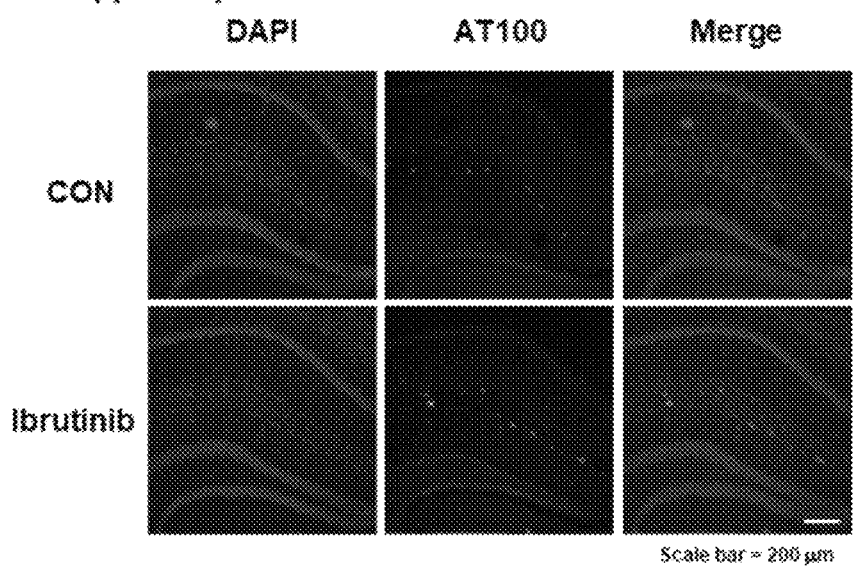
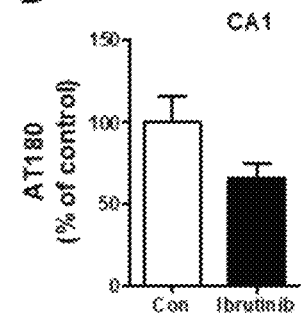
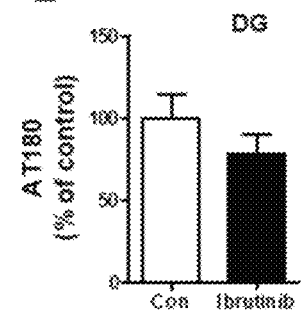

[fig. 27]
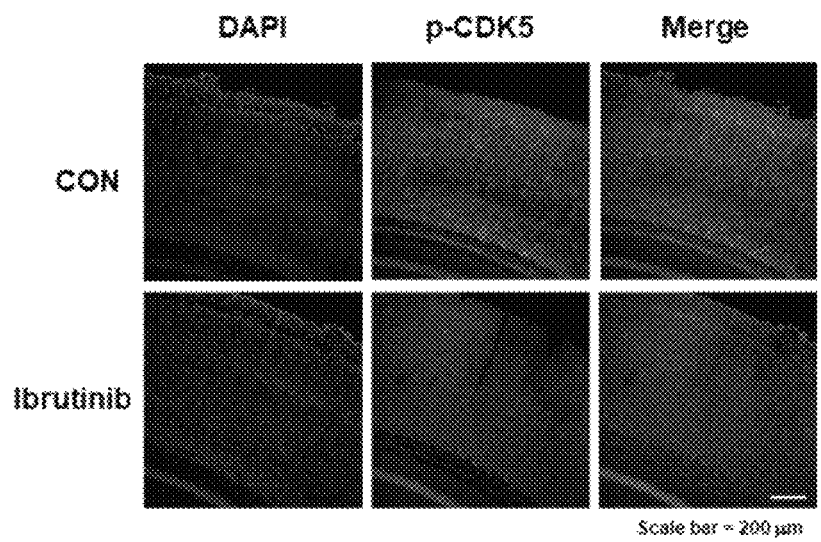
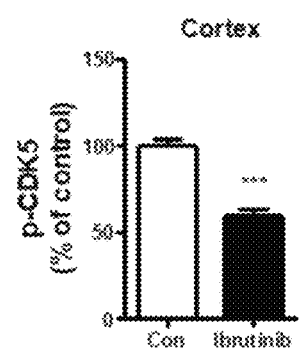
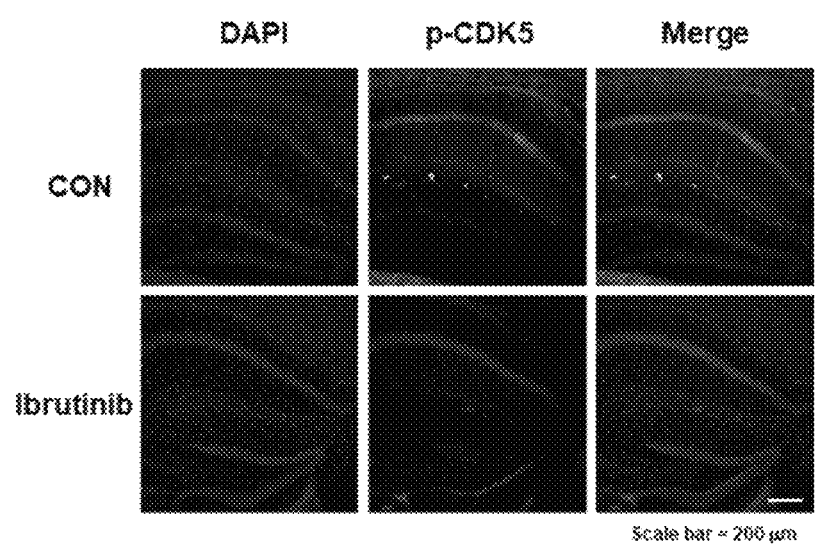
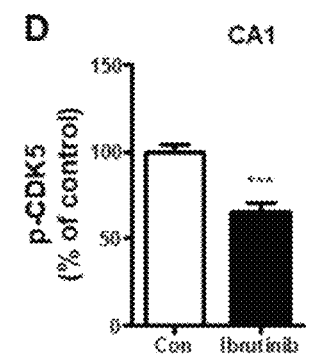
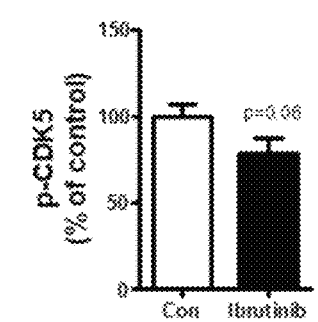

PHARMACEUTICAL COMPOSITION COMPRISING IBRUTINIB AS EFFECTIVE INGREDIENT FOR PREVENTING OR TREATING DEGENERATIVE BRAIN DISEASE

RELATED APPLICATIONS

This application is a 371 National Stage of International Patent Application No. PCT/KR2019/005063, entitled "PHARMACEUTICAL COMPOSITION COMPRISING IBRUTINIB AS EFFECTIVE INGREDIENT FOR PREVENTING OR TREATING DEGENERATIVE BRAIN DISEASE," filed Apr. 26, 2019, which claims priority to Korea Patent Application Nos. 10-2018-0049429, filed Apr. 27, 2018 and 10-2019-0048689, filed Apr. 25, 2019, all of which are herein incorporated by reference in their entireties.

TECHNICAL FIELD

The present disclosure relates to a pharmaceutical composition comprising ibrutinib as an active ingredient for prevention or treatment of degenerative brain disease.

BACKGROUND ART

Degenerative brain diseases refer to age-related diseases that occur in the brain and can be classified according to the main symptom and the affected brain area. Representative degenerative brain diseases include Alzheimer's disease, Parkinson's disease, and the like. Degenerative brain diseases are known to occur as a result of neuronal cell death due to neurodegeneration with age, and protein assemblies caused by genetic and environmental factors.

In addition, the death or degeneration of specific brain cells occurs temporally or progresses over a long period of time. Once dead, brain cells are not regenerated. Thus, the death of brain cells leads to the critical loss of brain functions, resulting in the onset of a degenerative brain disease. Particularly, cerebral dysfunction with the concomitant progressive inclination of cognitive, sensory, motor, and whole body functions brings about a change in personality and behaviors, finally driving the patients into an inability to take care of themselves. Main pathways of brain cell death include oxidative stress-induced oxidative toxicity, excitotoxicity, and apoptosis proposed, which cause cell death through respective specific signaling pathways. In detail, the oxidative damage to proteins, nucleic acids, and lipids by accumulated reactive oxygen species has been suggested as a main cause of brain cell death in patients with stroke, brain damage, Alzheimer's disease (AD), Parkinson's disease, and so on. In particular, the oxidative stress by free radicals is reported to be a main cause of cell death in each body tissue and suggested as one of the main mechanisms of cell death (Schapira, A. H., Curr. Opin. Neurol., 9(4):260-264, 1996).

In addition, microglia and astrocyte activation is involved in the onset and progression of neurodegenerative disease. As resident immune cells in the central nervous system (CNS), microglia are activated by external stimuli to induce immune reactions and inflammatory reactions. Microglia are a type of neuroglia responsible for a primary immune function in CNS. Microglia maintain the resting form composed of long branches and a thin cellular body in the absence of foreign material. In response to external or internal toxins, the ramified microglia can be transformed into the activated form composed of thick and short branches and a plump cellular body.

However, when activated by the bacterial endotoxin lipopolysaccharide (LPS), interferon-γ, amyloid beta, or ganglioside, microglia actively conduct phagocytosis and proliferate, unlike those in a normal state, and express cytokines, chemokines, iNOS (inducible nitric oxide synthase), and COX-2 (cyclooxygenase-2) to produce inflammation mediators. Because nitrogen monoxide (NO) synthesized by iNOS, prostaglandins synthesized by COX-2, and TNF-α have neurotoxicity, such microglial activation consequently aggravates neural damage while eliminating damaged cells and protecting neurons from external bacterial or viral infection. Hence, proper regulation of microglial activation may be a strategy for the treatment of degenerative brain disease.

Astrocytes are involved in the brain development process, but also in the homeostasis of cerebral activity. In the brain, astrocytes are found to aid neural activation by properly absorbing neural transmitters secreted from neurons and regulating ion concentrations. In addition, astrocytes play a critical role in the differentiation of neural stem cells to neurons.

When the brain is damaged, astrocytes actively grow, undergo swelling, and are pushed into a reactive phenotype termed astrogliosis. These reactive astrocytes are observed in the brains of patients with AIDS dementia, brain damage, ischemic brain disease, Alzheimer's disease, etc. That is, persistent activation of astrocytes results in neural cell death. Therefore, the proper regulation of astrocytic activation may also be a potential strategy for the therapy of degenerative brain diseases.

As of now, pharmacotherapy, surgery, and physiotherapy are used for treatment of degenerative brain diseases. Generally used for pharmacotherapy are drugs that function to supplement depleted dopamine in the brain and resolve the imbalance of neurotransmitters due to the insufficient dopamine, with the aim of preventing or delaying neurolysis and which control symptoms such as depression, etc.

However, these drugs do not aim at completely curing degenerative brain diseases, but at controlling symptoms because of inability to revive dead neural cells. There is therefore an urgent need for the development of a therapeutic agent that can more effectively prevent and treat degenerative brain disease.

Ibrutinib is known as an anticancer drug that targets B-cell malignant tumors and reported to inhibit the signal stimulating the uncontrollable growth and division of malignant tumor B cells. As such, ibrutinib was approved by the FDA on November, 2013 for the treatment of mantle cell lymphoma. In February, 2014, the FDA expanded the approved use of ibrutinib to chronic lymphocytic leukemia.

However, the possibility that ibrutinib might be used as a therapeutic agent for degenerative brain disease has not yet been proven thus far.

DETAILED DESCRIPTION OF THE INVENTION

Technical Problem

Leading to the present disclosure, thorough and inventive research, conducted by present inventors, resulted in the finding that ibrutinib can be used as a therapeutic agent for preventing or treating degenerative brain disease.

Therefore, a purpose of the present disclosure is to provide a pharmaceutical composition comprising ibrutinib or a pharmaceutically acceptable salt thereof as an active ingredient for prevention or treatment of degenerative brain disease.

Another purpose of the present disclosure is to provide a method for regulating activity of microglia or astrocytes, the method comprising a step of treating neuronal cells with ibrutinib or a pharmaceutically acceptable salt thereof in vitro.

A further purpose of the present disclosure is to provide a method for inhibiting LPS-induced microglial cell migration, the method comprising a step of treating neuronal cells with ibrutinib or a pharmaceutically acceptable salt thereof in vitro.

Technical Solution

In order to achieve the above purposes, the present disclosure provides a pharmaceutical composition comprising ibrutinib or a pharmaceutically acceptable salt thereof as an active ingredient for prevention or treatment of a degenerative brain disease.

In an embodiment of the present disclosure, the composition may inhibit microglial or astrocytic activity, thereby exhibiting an effect of suppressing damage of activated microglial cells or activated astrocytes to neuronal cells.

In an embodiment of the present disclosure, the composition may have inhibitory activity against microglial cell migration.

In an embodiment of the present disclosure, the microglial or astrocytic activity; or the microglial cell migration may be induced by LPS (lipopolysaccharides).

In an embodiment of the present disclosure, the composition may have inhibitory activity against amyloid plaque formation or tau protein phosphorylation.

In an embodiment of the present disclosure, the composition may increase a number of dendritic spines, a number of synaptophysin, and a number of puncta PSD-95 in neuronal cells.

In an embodiment of the present disclosure, the composition may improve long-term memory in an animal model of Alzheimer's disease.

In an embodiment of the present disclosure, the degenerative brain disease may be selected from the group consisting of Alzheimer's disease, Parkinson's disease, Huntington's disease, multiple sclerosis, multiple neuronal atrophy, epilepsy, encephalopathy, stroke, memory impairment, cognitive dysfunction, and learning impairment.

The present disclosure provides a method for inhibiting activity of microglial cells or astrocytes, the method comprising a step of treating neuronal cells with ibrutinib or a pharmaceutically acceptable salt thereof in vitro.

The present disclosure provides a method for inhibiting LPS-induced microglial cell migration, the method comprising a step of treating neuronal cells with ibrutinib or a pharmaceutically acceptable salt thereof in vitro.

Advantageous Effects

The present disclosure relates to a use of ibrutinib as a therapeutic agent for degenerative brain disease, wherein ibrutinib effectively inhibits microglial and astrocytic activity to downregulate the production of inflammatory cytokines, thereby suppressing inflammation, exhibiting an excellent neuroprotection against activated microglial cells and astrocytes, and inhibiting amyloid plaque formation and tau phosphorylation, which are causative of a degenerative brain disease. In addition, ibrutinib upregulates the expression level of the amyloid beta degrading enzyme IDE to suppress amyloid plaque formation and improve long-term memory in an animal model of Alzheimer's disease, and increases a population of dendritic spines associated with memory and learning to improve memory and learning, thereby preventing, alleviating, and treating neurodegenerative diseases. Therefore, ibrutinib can be advantageously used as an agent for prevention or treatment of degenerative brain disease.

BRIEF DESCRIPTION OF THE DRAWINGS

FIG. 1 shows whether or not ibrutinib exhibits toxicity toward microglial cells in terms of cell viability after treatment with ibrutinib at concentrations of 100, 250, 500, 750, and 1000 nM (1a) and 1, 5, 10, 25, and 50 μM (1b) and in terms of microscopic cell morphologies of LPS-stimulated BV2 microglial cells with or without pretreatment with ibrutinib (1c).

FIG. 2 shows expression levels of proinflammatory cytokines in BV2 microglial cells after pretreatment with ibrutinib as measured by RT-PCR (2a-2f), microscopic images of the cells stained with anti-CD11b and anti-COX-2 antibodies or anti-CD11b and anti-IL-1p antibodies (2g), and expression levels of IL-1β and COX-2 according to treatment with ibrutinib (2h and 2i).

FIG. 3 shows LPS-induced proinflammatory cytokine levels in BV2 microglial cells according to pretreatment with ibrutinib, as measured by RT-PCR (3a-3f).

FIG. 4 shows LPS-induced proinflammatory cytokine levels in primary microglial cells after pretreatment with ibrutinib, as measured by RT-PCR (4a-4f).

FIG. 5 shows LPS-induced proinflammatory cytokine levels in primary astrocytes after pretreatment with ibrutinib, as measured by RT-PCR (5a-5f).

FIG. 6 shows mRNA levels of L-1β and COX-2 in BV2 microglial cells upon treatment with the TLR4 inhibitor TAK242, ibrutinib, and LPS according to conditions, as measured by RT-PCR.

FIG. 7 shows analysis of the effect of ibrutinib on the ERK/AKT signaling in terms of ERK phosphorylation levels measured using antibodies to the ERK/AKT signaling in BV2 microglial cells after pretreatment with ibrutinib (7a-7c).

FIG. 8 shows AKT phosphorylation levels in BV2 microglial cells after pretreatment with ibrutinib (1 hour) (8a-8c), after pretreatment with ibrutinib for a longer period of time (5 hours) (8d-8f), and mRNA levels of COX-2 and IL-1beta in LPS-treated groups after pretreatment with ibrutinib (8g-8i).

FIG. 9 shows p-STAT3 levels in nuclear and cytosolic fractions obtained by subcellular fractionation of BV2 microglial cells pretreated with ibrutinib (1 μM), as measured by western blotting (9c-9d), microscopic images obtained by immunochemical staining with anti-p-STAT3 (s727) and anti-CD11b antibodies (9e), and p-STAT3 levels (9f).

FIG. 10 shows whether ibrutinib regulates LPS-stimulated microglial cell migration after cultured microglial cells are pretreated with ibrutinib and scratched, in terms of micrographic images of wound gap (10a) and counts of moved cells (10b).

FIG. 11 shows LPS-stimulated microglial activation and ibrutinib-induced inhibitory effect on microglial activation in the cortex and hippocampus in mouse models in terms of expression levels of the microglial cell marker IBa-1, as measured by immunohistochemical staining with an anti-IBa-1 antibody (11a-11c).

FIG. 12 shows LPS-stimulated astrocytic activation and ibrutinib-induced inhibitory effect on astrocytic activation in the cortex and hippocampus in mouse models in terms of expression levels of the astrocyte marker GFAP, as measured by immunohistochemical staining with an anti-GFAP antibody (12a-12c).

FIG. 13 shows data from a Y-maze test and novel object recognition test for analyzing memory and learning behaviors in animal models of Alzheimer's disease (5×FAD mice) according to treatment with ibrutinib (13A-13B).

FIG. 14 shows data from a Y-maze test and novel object recognition test for analyzing memory and learning behaviors in animal models of Alzheimer's disease (Tau-overexpressed PS19 mice) according to treatment with ibrutinib (14A-14B).

FIG. 15 shows the cognitive behavior improvement mechanism of ibrutinib (1 μM) in terms of dendritic spine counts in primary hippocampal neurons that have been transformed with GFP and then treated with ibrutinib (1 μM) or a vehicle for 24 hours, as analyzed by immunohistochemical staining (15A-15B).

FIG. 16 shows the cognitive behavior improvement mechanism of ibrutinib (5 μM) in terms of dendritic spine counts in primary hippocampal neurons that have been transformed with GFP and then treated with ibrutinib (1 μM) or a vehicle for 24 hours, as analyzed by immunohistochemical staining (16A-16B).

FIG. 17 shows the effect of ibrutinib on functional synapse in terms of numbers of puncta in primary hippocampal neurons that hat have been transformed with GFP, as analyzed by immunohistochemical staining with anti-synaptophysin and anti-PSD-95 antibodies (17A-17D).

FIG. 18 shows data from molecular mechanism studies on the cognitive behavior improvement of ibrutinib in primary hippocampal neurons that have been transformed with GFP, as analyzed by immunohistochemical staining with an anti-p-FAK antibody (18A-18B).

FIG. 19 shows effects of ibrutinib on populations of dendritic spines in normal mice that have been intraperitoneally injected with ibrutinib (10 mg/kg, i.p.) or a vehicle daily for two weeks, as analyzed by Golgi staining at hippocampus CA1 regions in the brains (19A-19D).

FIG. 20 shows effects of ibrutinib on populations of dendritic spines in animal models of Alzheimer's disease that have been intraperitoneally injected with ibrutinib (10 mg/kg, I.P) or a vehicle daily for two weeks, as analyzed by Golgi staining at hippocampus CA1 and cortical layer V regions (20A-20H).

FIG. 21 shows inhibitory effects of ibrutinib on amyloid plaque formation in the cortex and hippocampus of animal models of Alzheimer's disease (5×FAD), as analyzed by immunohistochemical staining with an anti-4G8 antibody (21A-21E).

FIG. 22 shows the inhibitory molecular mechanism of ibrutinib against amyloid plaque formation in the cortex and hippocampus of animal models of Alzheimer's disease (5×FAD), as analyzed by immunohistochemical staining with an anti-IDE antibody (22A-22E).

FIG. 23 shows effects of ibrutinib on total tau protein expression in the cortex and hippocampus of animal models of Alzheimer's disease (5×FAD), as analyzed by immunohistochemical staining with an anti-tau-5 antibody (23A-23E).

FIG. 24 shows effects of ibrutinib on tau phosphorylation in the cortex and hippocampus of animal models of Alzheimer's disease (5×FAD), as analyzed by immunohistochemical staining with an anti-AT8 antibody (24A-24E).

FIG. 25 shows effects of ibrutinib on tau phosphorylation in the cortex and hippocampus of animal models of Alzheimer's disease (5×FAD), as analyzed by immunohistochemical staining with an anti-AT100 antibody (25A-25E).

FIG. 26 shows effects of ibrutinib on tau phosphorylation in the cortex and hippocampus of animal models of Alzheimer's disease (5×FAD), as analyzed by immunohistochemical staining with an anti-AT180 antibody (26A-26E).

FIG. 27 shows effects of ibrutinib on p-CDK levels, which induce tau protein phosphorylation, in the cortex and hippocampus of animal models of Alzheimer's disease (5×FAD), as analyzed by immunohistochemical staining with an anti-p-CDK5 antibody (27A-27E).

BEST MODE FOR CARRYING OUT THE INVENTION

The present disclosure provides a pharmaceutical composition comprising ibrutinib or a pharmaceutically acceptable salt thereof as an active ingredient for prevention or treatment of degenerative brain disease.

As mentioned above, ibrutinib is known to be an anticancer drug that targets B-cell malignant tumors and it is reported that ibrutinib might be used for treating an immune disease. However, the possibility that ibrutinib might be used as a therapeutic agent for degenerative brain disease has not yet been proven thus far.

In the present disclosure, the availability of ibrutinib as a therapeutic agent for degenerative brain disease was first revealed.

According to an embodiment of the present disclosure, ibrutinib is found to inhibit microglial or astrocytic activation, thereby suppressing the damage of activated microglial cell or astrocytes to neurons. The present disclosure also reveals that ibrutinib effectively regulates activated microglial cell migration and as such, can suppress the onset of degenerative brain disease attributed to activated microglial cell migration.

As resident macrophages in the brain, microglial cells are important effector cells responsible for regulating the immune response in the central nervous system (CNS). When activated, the microglial cells play an important role in maintaining the CNS homeostasis by scavenging foreign matters such as drugs or toxins and secreting nerve growth factors. However, when becoming abnormally active in response to exposure to stresses such as signals from damaged neurons, deposition of aberrant proteins deformed by external stimuli, pathogenic infections, etc., microglial cells may induce neuronal injury, resulting in the onset of degenerative brain diseases such as Alzheimer's disease, Parkinson's disease, multiple sclerosis, cerebral infarction, etc. Therefore, regulation of abnormal microglial activation may be a novel therapeutic approach to degenerative brain disease.

Unlike microglia in a normal state, abnormally activated microglia actively perform phagocytosis, proliferate, and produce various inflammatory mediators including inflammatory cytokines such as TNF-α, IL-1μ, and IL-6, chemokines, iNOS (inducible nitric oxide synthase), COX-2 (cyclooxygenase-2), etc. Whereas having the advantage of phagocytizing damaged cells and protecting neurons from viral or bacterial infection, microglial activation induces neurotoxic responses by releasing proinflammatory cytokines and mediators such as iNOS that synthesizes nitrogen monoxide (NO), COX-2 that produces prostaglandins, TNF- α, and the like, resulting in aggravating neural damages and acting as a cause of degenerative brain disease.

In addition, astrocytes also play a pivotal role in maintaining normal brain activity and are particularly responsible for neuronal synaptic formation, synapse population control, synaptic functionality, and differentiation from neural stem cells to nerves. However, an excessive astrocytic response, that is, abnormal astrocytic activation causes neural death and induces the death of neighboring nerves, acting as a cause of degenerative brain disease. Therefore, regulation of abnormal astrocytic activation may also be a novel therapeutic approach to degenerative brain disease.

Examples of factors causing abnormal microglial and astrocytic activation include the bacterial endotoxin lipopolysaccharide (LPS), interferon-γ, amyloid beat, and gangliosides. In an embodiment of the present disclosure, lipopolysaccharide (LPS) may be preferably used.

In another embodiment of the present disclosure, ibrutinib was found to significantly inhibit LPS-induced expression levels of proinflammatory cytokines in BV2 microglial cells. Particularly, the inhibitory effects of ibrutinib on proinflammatory cytokines were characteristic according to types of neural cells. There were no observations of the inhibitory effects of ibrutinib on proinflammatory cytokines in primary astrocytes whereas ibrutinib effectively downregulated expression levels of proinflammatory cytokines such as COX-2 and IL-6 in microglial cells.

In addition, the present inventors examined the neuroprotective mechanism of ibrutinib, finding that ibrutinib inhibit interaction between TRL4 and LPS to regulate LPS-stimulated proinflammatory responses and that the regulatory effect of ibrutinib on proinflammatory responses depends on the AKT signaling.

Particularly for Parkinson's disease, which is a type of degenerative brain diseases, active interaction was observed between TRL4 and LPS in activated microglia, and AKT is involved in neuroinflammatory responses.

According to experiment results of the present disclosure, ibrutinib can effectively inhibit interaction between TRL4 and LPS and downregulate LPS-induced p-AKT (active AKT) levels in microglia, thereby decreasing or suppressing intracellular signaling pathways involved in the onset of degenerative brain diseases.

According to other experiment results for therapeutic effects on Alzheimer's disease in mouse models of Alzheimer's disease, ibrutinib upregulates the expression of the amyloid degrading enzyme IDE, thereby remarkably decreasing the number of amyloid plaques, which are causative of Alzheimer's disease. In addition, treatment with ibrutinib significantly decreased the phosphorylation of tau protein, which is causative of Alzheimer's disease, compared to non-treatment. Furthermore, in an embodiment of the present disclosure, a group treated with ibrutinib was found to increase in the number of dendritic spines and the number of synaptophysin or PSD-95 puncta (that is, functional synapses), and improve in long-term memory, compared to non-treated group.

Therefore, ibrutinib or a pharmaceutically acceptable salt thereof according to the present disclosure may be available as a therapeutic agent for a degenerative brain disease, and the present disclosure may provide a method for treatment of a degenerative brain disease, the method comprising a step of administering ibrutinib or a pharmaceutically acceptable salt thereof to a subject in need thereof.

The degenerative brain disease according to the present disclosure may be selected from the group consisting of Alzheimer's disease, Parkinson's disease, Huntington's disease, multiple sclerosis, multiple neuronal atrophy, epilepsy, encephalopathy, stroke, memory impairment, cognitive dysfunction, and learning impairment, but with no limitations thereto.

The composition for prevention or treatment of degenerative brain disease according to the present disclosure may comprise a pharmaceutically acceptable carrier. The composition comprising a pharmaceutically acceptable carrier may be in the form of various oral or parenteral formulations. When the composition is formulated, a typical diluent or excipient such as a filler, an extender, a binder, a humectant, a disintegrant, a surfactant, etc. may be employed.

Solid formulations for oral administration include a tablet, a pill, a powder, a granule, a capsule, etc., and these solid formulations may be prepared by mixing at least one compound with at least one excipient such as starch, calcium carbonate, sucrose, lactose, gelatin, etc. In addition to the simple excipient, a lubricant such as magnesium stearate, talc, etc. may also be used. Examples of liquid formulations for oral administration include a suspension, a liquid for internal use, an emulsion, a syrup, etc. In addition to a commonly used simple diluent such as water and liquid paraffin, various excipients such as a humectant, a sweetener, an aromatic, a preservative, etc. may also be contained.

Formulations for parenteral administration include a sterilized aqueous solution, a non-aqueous solution, a suspension, an emulsion, a lyophilized product and a suppository. The non-aqueous solution or suspension may contain propylene glycol, polyethylene glycol, a vegetable oil such as olive oil, an injectable ester such as ethyl oleate, etc. As a base of the suppository, witepsol, macrogol, tween 61, cocoa butter, laurin butter, glycerogelatin, etc. may be used.

The pharmaceutical composition may be in the form of a formulation selected from the group consisting of a table, a pill, a powder, a granule, a capsule, a suspension, a liquid for internal use, an emulsion, a syrup, a sterile aqueous solution, a non-aqueous solution, a suspension, an emulsion, a lyophilizate, and a suppository.

Moreover, the pharmaceutical composition may be administered in order to treat various diseases including neurodegeneration and/or symptoms associated therewith, as described above.

The composition of the present disclosure is administered in a pharmaceutically effective amount. As used herein, the term "pharmaceutically effective amount" refers to an amount sufficient to treat a disease at a reasonable benefit/risk ratio applicable to a medical treatment. The effective dosage level of the composition may be determined depending on the subject's type, the disease severity, the subject's age and sex, the activity of the drug, sensitivity to the drug, the time of administration, the route of administration, excretion rate, the duration of treatment, drugs used in combination with the composition, and other factors known in the medical field.

The pharmaceutical composition of the present disclosure may be administered alone or in combination with other therapeutic agents, and may be administered sequentially or simultaneously with conventional therapeutic agents. The composition can be administered in a single or multiple dosage form. It is important to administer the composition in the minimum amount that can exhibit the maximum effect without causing side effects, in view of all the above-described factors. The pharmaceutical composition of the present disclosure may be administered at a dose ranging from 0.001 to 100 mg/kg for adults.

So long as it reaches a target tissue, any general route may be taken for administering the pharmaceutical composition.

According to purposes, the composition of the present disclosure may be administered intraperitoneally, intravenously, intramuscularly, subcutaneously, intradermally, orally, intranasally, intrapulmonarily or intrarectally, but with no limitations thereto. In addition, the composition may be administered using any system capable of delivering the active ingredient to a target cell.

In order to prevent and treat a degenerative brain disease, the composition of the present disclosure may be used alone or in combination with surgery, hormonal therapy, pharmaceutical therapy, and a biological reaction regulator.

The present disclosure may provide a method for inhibiting activity of microglia or astrocytes, the method comprising a step of treating neuronal cells with ibrutinib or a pharmaceutically acceptable salt thereof, in vitro.

The present disclosure may provide a method for inhibiting LPS-induced microglial cell migration, the method comprising a step of treating neuronal cells with ibrutinib or a pharmaceutically acceptable salt thereof, in vitro.

The present disclosure may provide a method for suppressing amyloid plaque formation or tau phosphorylation or improving long-term memory, the method comprising a step of treating neuronal cells with ibrutinib or a pharmaceutically acceptable salt thereof, in vitro.

MODE FOR CARRYING OUT THE INVENTION

Below, the present disclosure will be described in detail with reference to the following Examples. The Examples are provided by way of illustration only and not by way of limitation. Those of skill in the art will readily recognize a variety of noncritical parameters that could be changed or modified to yield essentially similar results.

Preparation Examples and Experimental Methods

Cell Lines and Culture Conditions

BV2 microglial cells (a generous gift from Dr. Kyung-Ho Suk) were maintained in high-glucose DMEM (Invitrogen, Carlsbad, Calif., USA) supplemented with 5% fetal bovine serum (FBS, Invitrogen, Carlsbad, Calif., USA) in a 5% $CO_2$ incubator.

Wild-Type Mice

All experiments were performed in accordance with approved animal protocols and guidelines established by the Korea Brain Research Institute (IACUC-2016-0013). C57BL6/N mice were purchased from Orient-Bio Company. Male C57BL6/N mice (8 weeks old, 25-30 g) were housed in a pathogen-free facility with 12 hours/12 hours light and dark cycle per day at the ambient temperature of 22° C. The wild-type mice were intraperitoneally (i.p.) administered ibrutinib (10 mg/kg) or vehicle (DMSO) for 3 days and subsequently injected with LPS (10 mg/kg, i.p.) for three hours. Three hours after the injection, the mice were perfused and fixed with 4% paraformaldehyde (PFA) solution, and the brain tissues were flash-frozen and sliced into 40-mm-thick sections using a cryostat. Each brain section was processed for immunohistochemical staining. The brain sections were rinsed with PBS and permeabilized with PBS containing 0.2% Triton X-100 and 0.5% BSA for 1 hour at room temperature. Then, the tissue sections were incubated overnight at 4° C. with primary antibodies and washed with 0.5% BSA three times and incubated with a biotin-conjugated anti-rabbit secondary antibody (1:400, Vector Laboratories) for 1 hour at room temperature. Subsequently, the sections were rinsed with 0.5% BSA and incubated in an avidin-biotin complex solution (Vector Laboratories, Burlingame, Calif.) for 1 hour at room temperature. After washing the sections three times with 0.1 M phosphate buffer (PB), the signal was detected by incubating the sections with 0.5 mg/ml 3,3'-diaminobenzidine (DAB, Sigma-Aldrich) in 0.1 M PB containing 0.003% $H_2O_2$. The sections were rinsed with 0.1 M PB and mounted on gelatin-coated slides, and images were captured under a bright-field microscope (Leica).

Construction of Mouse Model with Alzheimer's Disease (5×FAD Mice)

F1 generation 5×FAD mice (stock number 008730, B6SJL-Tg APPSwF1Lon, PSEN1*M146L*L286V6799Vas/Mmjax) were purchased from the Jacson Lab. Transgenic male mice (5×FAD) were housed together with female C57BL/6J mice purchased from the Jacson Lab. 5×FAD is known to overexpress two familial Alzheimer's disease (FAD) mutant human proteins: APP (695) with K670N, M671L (Swedish), I716V (Florida), and V717I (London) FAD mutations and PS1 with two FAD mutations (M146L and L286V). The transgenes were overexpressed in the brain under the mouse Thy1 promoter, and genotyping for 5×FAD transgenes was performed with PCR according to the genotyping protocol provided by the Jackson Lab.

Genotyping of 5×FAD Mice

Tails were excised from 4-week-old mice and genomic DNAs were extracted therefrom. Briefly, tail samples were incubated at 95° C. for 2 hours in an alkaline lysis solution, followed by reaction termination with a neutralizing solution. PCR was performed using Prime Taq Premix (GeNetBio, Korea). The PCR products were separated on 1.5% agarose gel by electrophoresis. Primer sequences used in this assay were as follows:

```
Forward primer:
5-AATAGAGAACGGCAGGACCA-3 reverse primer:
5-GCCATGAGGGCACTAATCAT-3
```

PCR was carried out with 35 cycles of denaturation at 94° C. for 30 seconds, annealing at 60° C. for 30 seconds, and extension at 72° C. for 90 seconds. The PCR products were separated, together with Eco Dye (1:5000, Korea), on 1.5% agarose gel by electrophoresis.

Immunohistochemistry and Immunofluorescence Assay

The mouse animals used in the experiments were perfused and fixed with perfusion solution (0.9% NaCl, Sigma) and 4% paraformaldehyde solution (Millipore), and the brain tissues were sliced using a cryostat (Leica) (40 mm thick). Each brain section was processed for immunofluorescence and immunohistochemical staining. In this regard, the brain sections were rinsed with PBS and incubated with the following primary antibodies: an anti-4G8 antibody for detecting amyloid plaques; an anti-IDE antibody, which is an antibody to an amyloid degrading enzyme; and an anti-AT8 antibody for detecting Tau phosphorylation. The antibodies were diluted in PBS containing 0.5% BSA. The incubation was conducted overnight at 4° C. while mildly shaking. On the next day, the tissues were rinsed with PBS containing 0.5% BSA and then incubated at room temperature for 1 hour with 555-conjugated anti-rabbit IgG (1:200, Molecular Probe). The tissues were mounted in DAPI-containing mounting solution (Vector Laboratories) on gelatin-coated cover glass, and images of the stained tissues were captured using a confocal microscope (Nikon, Japan). For immunohistochemistry, the brain sections were rinsed with PBS, incubated, and permeabilized with PBS containing 0.2% Triton X-100 and 1% BSA for 1 hour at room temperature. The tissue sections were subsequently incubated at 4° C. overnight with the primary antibodies while mildly shaking. On the next day, the tissue sections were washed three times with PBS containing 0.5% BSA and incubated at room temperature for 1 hour with the following secondary antibody: a biotin-conjugated anti-rabbit antibody (1:400, Vector Laboratories). The sections were then rinsed with PBS containing 0.5% BSA and incubated in an avidin-biotin complex solution for 1 hour at room temperature. After washing the sections three times with 0.1 M phosphate buffer (PB), the signal was detected by incubating the sections with 0.5 mg/ml 3,3'-diaminobenzidine (DAB, Sigma) in 0.1 M PB containing 0.003% $H_2O_2$. The sections were rinsed with 0.1 M PB and mounted on gelatin-coated slides, and images were captured under a bright-field microscope (Leica).

Antibodies and Inhibitors

Used in the experiments were the following primary antibodies: rat-anti-mouse CD11b (1:400, Abcam), rabbit-anti-COX2 (1:1000, abcam), rabbit-anti-IL-1b (1:200, abcam), rabbit-anti-GFAP (1:5000, neuromics), rabbit-anti-Iba1 (1:1000, Wako), goat-anti-Iba1 (1:500, Wako), rabbit-anti-AKT (1:1000, Santa Cruz), p-AKT(Ser473, Thr308) (1:1000, Cell Signaling), rabbit-anti-ERK (1:1000, Santa Cruz), rabbit-anti-p-ERK (Thr42/44) (1:1000, Cell Signaling), rabbit-anti-STAT3 (1;1000, Cell Signaling), rabbit-anti-p-STAT3 (Ser727, abcam), mouse-anti-synaptophysin (1:200, Sigma), mouse-anti-PSD95 (1:200, Neuromab), rabbit-anti-pFAK (1:500, Cell signaling), mouse-anti-4G8 (1:500, Biolegend), rabbit-anti-IDE (1:200, Abcam), rabbit-anti-NEP (1:200, Millipore), mouse-anti-Tau5 (1:200, Invitrogen), mouse-anti-AT8 (1:200, Invitrogen), mouse-anti-AT100 (1:200, Invitrogen), mouse-anti-180 (1:200, Invitrogen), rabbit-anti-pCDK5 (1:200, Biosource). In addition, inhibitors used included TLR4 inhibitor (TAK-242, 500 nM), and AKT inhibitor (MK2206, 10 mM).

MTT Assay

Cell viability was assessed using the 3-(4,5-dimethylthiazol-2-yl)-2,5-diphenyltetrazolium bromide (MTT) assay. Cells were seeded into 96-well plates and treated with various concentrations of ibrutinib (100 nM-1 µM, 1 µM-50 µM) for 24 hours in the presence or absence of FBS. The cells were then treated with 0.5 mg/ml MTT and incubated for 3 hours at 37° C. in a 5% $CO_2$ incubator. Absorbance was read at 580 nm.

Primary Microglial and Astrocyte Cultures

Primary mixed glial cells were cultured from the cerebral cortices of 1-day-old Sprague-Dawley rats. In brief, the cortices were triturated into single cells in high-glucose DMEM containing 10% FBS and a penicillin-streptomycin solution (5000 units/ml penicillin, 5 mg/ml streptomycin, Corning, USA) and plated into 75-cm² T culture flasks (0.5 hemisphere/flask) for 2 weeks. To harvest microglial cells, the plate were shaken continuously at 120 rpm for 2 hours. The fluid medium was subsequently collected and centrifuged at 1500 rpm for 15 min, and the cell pellets were resuspended at a density of $1 \times 10^5$ cells per well to 24-well plates. Once the microglial cells were collected, the remaining cells in the flask were harvested using 0.1% trypsin to obtain primary astrocytes. These primary astrocytes and primary microglial cells were cultured in 12-well plates (35 mm) pre-coated with poly-D-lysine (Sigma) before use in experiments.

RT-PCR

Total RNA was extracted using TriZol (Invitrogen) according to the manufacturer's instructions. Total RNA was reverse transcribed into cDNAs using a Superscript cDNA Premix Kit II with oligo-dT primers (GeNetBio, Korea). RT-PCR was performed using Prime Taq Premix (GeNetBio, Korea). The RT-PCR products were separated by electrophoresis on 1.5% agarose gels containing Eco Dye (1:5000, Korea). Images of the PCR products were analyzed using ImageJ (NIH) and Fusion software (Korea).

Immunocytochemistry

BV2 microglial cells were fixed with 4% paraformaldehyde for 10 minutes, washed with PBS three times, and then incubated overnight at 4° C. with anti-CD11b and anti-IL-1β, or anti-CD11b and anti-COX-2 antibodies in GDB buffer (0.1% gelatin, 0.3% Triton X-100, 16 mM sodium phosphate, pH 7.4, and 450 mM NaCl). On the next day, the cells were washed with PBS three times and incubated with secondary antibodies for 1 hour at room temperature. Alexa Fluor 488-conjugated anti-mouse and Alexa Fluor 555-conjugated anti-rabbit (1:200, Molecular Probes, USA) were used as the secondary antibodies. Thereafter, images were captured from a single plane using a confocal microscope (Nikon, Japan) and analyzed using ImageJ software.

Western Blotting

To examine whether ibrutinib affects ERK/AKT signaling to alter neuroinflammation, BV2 microglial cells were treated with ibrutinib (1 µM) or vehicle for 1 hour, followed by LPS (1 µg/ml) or PBS for 45 min. Thereafter, the cells were lysed with RIPA buffer containing protease and phosphatase inhibitors (Roche, USA). Western blot analyses were performed in a conventional manner, and images were analyzed using Fusion software or ImageJ software.

Wound Healing Assay

BV2 microglial cells were seeded into 12-well plates and cultured to 80-90% confluency. The cells were scratched with a cell scratcher (SPL, Korea) to create a wound. Immediately after scratching, images were captured. Subsequently, the cells were treated with ibrutinib (500 nM) or vehicle for 1 hour, followed by LPS or PBS for 24 hours. Images were then captured again to assay wound healing.

Cytosol and Nuclear Fractionation

BV2 microglial cells were lysed in cytosol fractionation buffer (10 mM HEPES, pH 8.0, 1.5 mM $MgCl_2$, 10 mM KCl, 0.5 mM DTT, 300 mM sucrose, 0.1% NP-40, and 0.5 mM PMSF). After 5 min, the cell lysates were centrifuged at 10,000 rpm for 1 min at 4° C., and the supernatant was stored as the cytosolic fraction. The pellet was lysed in nuclear fractionation buffer (10 mM HEPES, pH 8.0, 20% glycerol, 100 mM KCl, 100 mM NaCl, 0.2 mM EDTA, 0.5 mM DTT, and 0.5 mM PMSF) on ice for 15 min. Afterwards, the sample was centrifuged at 10,000 rpm for 15 min at 4° C. Western blot analyses were performed with antibodies to STAT3 (s727), PCNA, and β-actin and the blots were analyzed using Fusion software.

Y-Maze Test

To assess whether the administration of ibrutinib increases short-term memory in wild-type mice or an animal model of Alzheimer's disease (5×FAD mice, PS19 mice), a Y-maze test was performed. In a Y-shaped maze with three arms at angles of 120° from each other, each having the dimensions of 42 cm length×3 cm width×12 cm height, a mouse was positioned at the end of one arm. During a 5-minutes trial, the number of arms visited and their sequences were recorded. Thereafter, percent alternation= (number of alteration/number of triads)×100 was calculated and used as an index for short-term memory.

alteration: 1 point acquired when entering the three different arms sequentially.

triads: total number of arm entries-2

Novel Object Recognition Test

To assess whether the administration of ibrutinib improves long-term memory in wild-type mice or an animal model of Alzheimer's disease (5×FAD mice, PS19 mice), mice were placed at the center of an experimental apparatus (42×42×25 cm) in which two objects identical in shape and size were positioned at respective corners. The mice moved freely to explore the objects for 5 minutes under video recording. After 24 hours, one of the two objects was changed with a new one. The times during which the mouse had made access to the familiar and new objects were measured, respectively. Preference for the novel object was analyzed and used as an index for long-term memory.

Statistical Analyses

All data were analyzed with GraphPad Prism 4 software using either unpaired two-tailed T tests or ANOVA. Post hoc analyses were performed with Tukey's multiple comparison test with significance set at *$p<0.05$. Data are presented as the mean±SEM (*$p<0.05$, $p<0.01$, and *$p<0.001$).

Example 1

Assay for Cytotoxicity of Ibrutinib Toward BV2 Microglial Cells

To examine whether ibrutinib has a toxic effect on BV2 microglial cells, BV2 microglial cells were treated with vehicle or ibrutinib (100, 250, 500, 750, or 1000 nM) for 24 hours, and MTT assays were conducted. In addition, higher doses of ibrutinib on cell viability were examined. In this regard, BV2 microglial cells were treated with vehicle or ibrutinib (1, 5, 10, 25, or 50 μM) for 24 hours, and MTT assays were conducted.

It was found that ibrutinib did not induce cytotoxicity in BV2 microglial cells at concentrations up to 25 μM, as shown in FIG. 1. On the other hand, cell death was detected at 50 μM. Consequently, ibrutinib does not exert toxic effects on microglial cells at concentrations up to 25 μM (see FIGS. 1a-1b).

To determine whether ibrutinib alters the LPS-induced morphology of BV2 microglial cells, cells were pretreated with ibrutinib (1 μM) or vehicle for 30 minutes, followed by treatment with LPS (1 μg/ml) or PBS for 5.5 hours. The cells were fixed and then immunostained with an anti-CD11b antibody.

As can be seen in FIG. 1c, LPS-treated BV2 microglial cells displayed long thin branches extending from the cellular body. Pretreatment with ibrutinib followed by LPS treatment reduced the number of long thin branches extending from the cellular body (see FIG. 1c).

Example 2

Regulatory Effect of Ibrutinib on LPS-Induced Proinflammatory Cytokine Level

BV2 microglial cells were treated with 1 μM of ibrutinib for 30 min, followed by LPS (1 μg/ml) or PBS for 5.5 hours. Then, RNA was isolated, and proinflammatory cytokine levels were measured using RT-PCR. In this regard, mRNA levels of inflammatory cytokines IL-1p, COX-2, IL-6, and TNF-α were measured.

As can be seen in FIG. 2, treatment with ibrutinib reduced the mRNA levels of the LPS-induced proinflammatory cytokines IL-1β, COX-2, IL-6, and TNF-α, with the expression reduction of iNOS to a lesser extent (FIGS. 2a-2f).

In addition, the present inventors re-assessed the RT-PCR data through immunocytochemistry. The cells were immunostained with anti-CD11b and anti-COX-2 antibodies or with anti-CD11b and anti-IL-1β antibodies. In addition, microglial cells treated with a vehicle were used as a control.

As is understood from the data of FIGS. 2g-2i, ibrutinib reduced LPS-induced COX-2 and IL-1β levels.

Therefore, the data imply that ibrutinib suppresses inflammatory responses in BV2 microglial cells.

Examination was made to see whether post-treatment with ibrutinib induces the downregulation of inflammatory cytokines in microglial cells like the pretreatment. In this regard, BV2 microglial cells were treated with LPS (1 mg/ml) or PBS for 30 min, followed by ibrutinib (1 mM) for 5.5 hours. Then, RT-PCR was performed.

As a result, post-treatment with ibrutinib also significantly decreased the mRNA levels of IL-6 alone, unlike the result of FIG. 2 (see FIG. 3).

Example 3

Suppressive Effect of Ibrutinib on Proinflammatory Cytokine Levels in Primary Microglial Cells To determine whether ibrutinib regulates inflammatory responses in primary microglial cells and astrocytes, microglial cells were treated with vehicle or ibrutinib (1 μM) for 30 min, followed by LPS (1 μg/ml) or PBS for 5.5 hours. Inflammatory cytokine levels were then measured by RT-PCR.

As a result, pretreatment with ibrutinib significantly downregulated levels of the proinflammatory cytokines COX-2 and IL-6, compared to other cytokines (see FIGS. 4a-4f).

In addition, the present inventors examined whether ibrutinib also affects proinflammatory cytokine levels in primary astrocytes. Primary astrocytes were treated with vehicle or ibrutinib (1 μM) for 30 min, followed by LPS (1 μg/ml) or PBS for 5.5 hours. Proinflammatory cytokine levels were measured by RT-PCR.

Interestingly, ibrutinib did not reduce the levels of proinflammatory cytokines in primary astrocytes (see FIG. 5). These data indicate that ibrutinib selectively affects proinflammatory responses depending on the cell type.

Example 4

Suppressive Effect of Ibrutinib on LPS-Induced Proinflammatory Cytokine Levels by Regulating TLR4

LPS is known to interact with TLR4 on the surface of microglial cells. Thus, examination was made to see whether ibrutinib inhibits the LPS/TLR4 interaction on the cell surface to regulate neuroinflammatory responses. In this regard, BV2 microglial cells were pretreated with TAK242 (TLR inhibitor, 500 nM) or vehicle for 30 min, followed by treatment with ibrutinib (1 μM) or vehicle for 30 min and subsequent treatment with LPS (1 μg/ml) or PBS for 5 hours. Total RNA was isolated, and IL-1β and COX-2 mRNA levels were measured by RT-PCR.

Analysis results showed that ibrutinib significantly decreased LPS-induced COX-2 and IL-1β mRNA levels in BV2 microglial cells (FIGS. 6a-6c). In addition, the regulation of TLR4 further reduced LPS-induced IL-1β and COX-2 mRNA levels in BV2 microglial cells in the presence of ibrutinib (see FIGS. 6a-6c).

These data indicate that ibrutinib inhibits interactions between TLR4 and LPS to alter LPS-stimulated proinflammatory responses.

Example 5

Assay of Ibrutinib for Altering AKT Signaling to Modulate LPS-Induced Proinflammatory Responses Recent studies reported that AKT and ERK signaling plays important roles in modulating proinflammatory cytokine levels in glial cells (REF). In order to examine whether ibrutinib plays a role in modulating LPS-mediated neuroinflammatory responses, the action of ibrutinib on the ERK/AKT signaling was analyzed. To this end, BV2 microglial cells were pretreated with ibrutinib (1 µM) or vehicle for 1 hour, followed by treatment with LPS (1 µg/ml) or PBS for 45 min, and western blotting was conducted with antibodies to the ERK/AKT signaling to detect changes in the expression levels of factors involved in the signaling.

Unexpectedly, ibrutinib did not reduce the LPS-mediated increases in p-ERK levels in BV2 microglial cells (see FIGS. 7a-7c). However, it was observed that ibrutinib remarkably reduced the LPS-induced increases in p-AKT levels in BV2 microglial cells (FIGS. 8a-8c).

Based on the above result, an examination was made to see whether ibrutinib modulates AKT signaling to alter LPS-induced inflammatory responses. To this end, BV2 microglial cells were pretreated with ibrutinib (1 µM) or vehicle for 5 hours, followed by treatment with LPS (1 µg/ml) or PBS for 45 min. Western blotting was conducted with an anti-p-AKT antibody.

As a result, treatment with ibrutinib for a longer time significantly reduced LPS-induced p-AKT levels (see FIGS. 8d-8f).

In addition, the present inventors examined whether ibrutinib modulates inflammatory responses through the AKT signaling. In this regard, BV2 microglial cells were pretreated with the MK2206 (a AKT inhibitor, 10 µM) or vehicle for 30 min, treated with ibrutinib (1 µM) or vehicle for 30 min, treated with LPS (1 µg/ml) or PBS for 5 hours, and mRNA levels of COX-2 and IL-1β were measured by RT-PCR.

Consistent with the results obtained above, the groups treated with ibrutinib and LPS decreased in the mRNA levels of COX-2 and IL-1β (see FIGS. 8g-8i). In addition, treatment with MK2206, Ibrutinib, and LPS significantly suppressed mRNA levels of COX-2 and IL-1beta compared with treatment with LPS and MK2206 (see FIGS. 8g-8i). These data indicate that the effects of ibrutinib on proinflammatory responses depend on AKT signaling

Example 6

Reducing Effect of Ibrutinib on LPS-Stimulated p-STAT3 Levels in Nucleus

The transcription factor signal transducer and activator of transcription 3 (STAT3) is known to play an important role in regulating LPS-induced proinflammatory cytokine levels. An examination was made to see whether ibrutinib needs STAT3 to alter inflammatory responses. In this regard, BV2 microglial cells were treated with ibrutinib (1 µM) or vehicle for 30 min, followed by treatment with LPS (1 µg/ml) or PBS for 5.5 hours. Subcellular fractionation was conducted.

Data analysis showed that ibrutinib reduced the LPS-stimulated increases in nuclear p-STAT3 (Ser727) levels (FIGS. 9a-9b), with cytosolic p-STAT3 levels tending toward a decrease (see FIGS. 9c-9d).

In order to evaluate the results above obtained, immunocytochemistry was performed with anti-p-STAT3 (s727) and anti-CD11b antibodies. Ibrutinib was observed to downregulate LPS-induced nuclear p-STAT3 levels (see FIGS. 9e-9f). These data suggest that ibrutinib alters neuroinflammatory responses in an STAT3-dependent manner.

Example 7

Assay for Suppressive Effect of Ibrutinib on BV2 Microglial Cell Migration

An examination was made to see whether ibrutinib regulates LPS-stimulated microglial cell migration. To this end, cells were treated with ibrutinib (500 nM) or vehicle for 23.5 hours and then with LPS (100 ng/ml) or PBS for 30 min before a wound-healing assay in which the influence of ibrutinib cell migration to scratched regions on the culture plate was analyzed.

As a result, ibrutinib significantly decreased LPS-stimulated microglial cell migration compared with LPS treatment (see FIGS. 10a-10b).

These data showed the ability of ibrutinib to inhibit LPS-induced neuronal cell migration, implying that ibrutinib can suppress the neural cell migration-induced onset of degenerative brain disease or treat degenerative brain diseases.

Example 8

Assay for Inhibitory Effect of Ibrutinib on LPS-Stimulated Microglial and Astrocyte Activation in Mouse Model Recent studies reported that activated microglia and astrocytes are associated with the onset of degenerative brain disease. Thus, in order to examine whether ibrutinib can be used as a therapeutic agent for degenerative brain disease, an examination was made of the effects of ibrutinib on LPS-induced microglial and astrocytic activation in animal models. To this end, ibrutinib was intraperitoneally injected to wild-type mice (10 mg/kg/day) for 3 days, after which immunohistochemistry was conducted with anti-IBa-1 (FIGS. 11a-11c) or anti-GFAP antibodies (FIGS. 12a-12c).

LPS injection was observed to upregulate microglial and astrocytic activation in wild-type mice whereas ibrutinib injection significantly decreased microglial and astrocytic activation. Therefore, the data indicate that ibrutinib can regulate LPS-induced microglial and astrocytic activation, suggesting that suppression of the cell activation may lead to the prevention or treatment of degenerative brain disease.

Example 9

Assay for Behavior Change Associated with Memory and Learning in Animal Model of Alzheimer's Disease According to Treatment with Ibrutinib To examine what influence ibrutinib has on memory and learning, animal models of Alzheimer's disease (5xFAD, PS19 mice) were administered ibrutinib (10 mg/kg, i.p.) or a vehicle for 14 days and then subjected to Y-maze test for assessing short-term memory behavior and to a novel object recognition test (NOR) for assessing long-term memory behavior.

As a result, the Alzheimer's disease animal model 5xFAD mice treated with ibrutinib were observed to remarkably improve in long-term memory (FIGS. 13A-13B), and the Alzheimer's disease animal model PS19 mice treated with ibrutinib tended to increase in long-term memory (see FIGS. 14A-14B).

Therefore, these results indicate that ibrutinib increases learning and memory in animal models of Alzheimer's disease.

Example 10

Assay for Promotive Effect of Ibrutinib on Population Increase and Formation of Dendritic Spine in Primary Hippocampal Neurons To analyze the cognitive behavior improving mechanism of ibrutinib, GFP was transfected into primary hippocampal neurons which were then treated 1 or 5 µM of ibrutinib for 24 hours. Subsequently, dendritic spines were monitored for population change. After being immunostained with antibodies to the pre-synaptic marker synaptophysin and the post-synaptic marker PSD-95, the cells were measured for numbers of puncta and expression levels.

As a result, ibrutinib 1 μM and 5 μM both significantly increased the population of dendritic spines in primary hippocampal neurons, compared with the vehicle (FIGS. 15A-15B and 16A-16B), with a remarkable increase of the population of synaptophysin and PSD-95 puncta in the ibrutinib 5 μM-treated group, compared to the vehicle treated group (FIGS. 17A-17D). Therefore, ibrutinib was observed to improve cognitive behavior by increasing functional synapses in the hippocampus.

Example 11

Study on Molecular Mechanism of Ibrutinib-Induced Dendritic Spine Population Increase in Primary Hippocampal Neurons To assay the memory behavior improvement mechanism of ibrutinib, GFP was transfected into primary hippocampal neurons which were then treated with ibrutinib 5 μM or a vehicle for 24 hours. After being immunostained with an antibody to p-FAK, which is involved in modulating the population of dendritic spines, the cells were measured for the expression level of p-FAK.

As a result, ibrutinib 5 μM was observed to remarkably downregulate p-FAK expression, compared to the vehicle (FIGS. 18a-18b). Therefore, ibrutinib modulates numbers of dendritic spines by inhibiting the FAK signaling.

Example 12

Assay for Ibrutinib-Induced Population Increase of Dendritic Spines in Wild-Type Mice and Animal Model of Alzheimer's Disease To assay the cognitive behavior improvement mechanism of ibrutinib, ibrutinib was i.p, injected at a dose of 10 mg/kg for 14 days into wild-type mice and the animal model of Alzheimer's disease PS19 mice (3 months old). The brains were excised and subjected to Golgi staining before analyzing numbers of spines in the cortex and hippocampal neurons (AO region, BS position).

Ibrutinib increased the number of spines of hippocampus CA1 neurons in the wild-type mice, compared to the vehicle (FIGS. 19A-19D). The animal model of Alzheimer's disease (PS19 mice) was also observed to increase in the number of spines of hippocampal neurons when treated with ibrutinib, compared to the vehicle (FIGS. 20A-20D). In contrast, no significant changes in the number of spines of cortical layer V neurons were observed between the ibrutinib-treated animal model of Alzheimer's disease and the vehicle-treated group (FIGS. 20E-20H). Therefore, ibrutinib improved cognitive function in vivo by increasing dendritic spine densities.

Example 13

Assay for Inhibitory Effect of Ibrutinib on Plaque Formation in Animal Model of Alzheimer's Disease To examine whether ibrutinib can be used as a therapeutic agent for degenerative brain disease, animal models of Alzheimer's disease were analyzed for numbers of amyloid plaques and expression levels of the amyloid degrading enzymes IDE and NEP after treatment with ibrutinib.

To this end, mice of Alzheimer's disease (5×FAD mice) were injected with ibrutinib (10 mg/kg, i.p) or a vehicle for 14 days and subjected to immunohistochemical staining with an anti-4G8 antibody and an anti-IDE antibody followed by microscopic observation.

As shown in FIG. 21, ibrutinib remarkably reduced amyloid plaques compared to the vehicle as measured by the immunohistochemical staining with the anti-4G8 antibody capable of detecting amyloid (FIGS. 21A-21E). In addition, a molecular mechanism in which ibrutinib reduces amyloid plaques was examined. First, the expression level of the amyloid degrading enzyme IDE was measured. As shown in FIG. 21, ibrutinib increased expression levels of the amyloid degrading enzyme IDE in both the cortex and the hippocampus, compared to the vehicle (FIGS. 22A-22E). These data imply that ibrutinib can inhibit amyloid plaques, which are a cause of Alzheimer's disease, by increasing expression levels of IDE.

Example 14

Assay for Ibrutinib-Induced Modulation of Tau Phosphorylation in Mouse Model of Alzheimer's Disease To examine whether ibrutinib can be used as a therapeutic agent for degenerative brain disease, ibrutinib was analyzed for ability to modulate tau phosphorylation. In this regard, the animal model of Alzheimer's disease 5×FAD (3 months old) was monitored for tau expression levels and phosphorylation after being treated with ibrutinib. Briefly, Alzheimer's disease-induced mice were injected with ibrutinib (10 mg/kg, i.p) or a vehicle for 14 days and subjected to immunohistochemical staining with anti-Tau5, anti-CDK, anti-AT8, anti-AT100, and anti-AT180 antibodies, followed by microscopic observation.

As can be seen in FIG. 23, there were no significant difference in tau-5 expression in the cortex and hippocampus of 5×FAD between treatment with ibrutinib or the vehicle as measured by immunohistochemical staining with the anti-tau5 antibody capable of detecting total tau (FIGS. 23A-23E). FIGS. 24 to 26 shows results of immunohistochemical staining with anti-AT8, anti-AT100, and anti-AT180 antibodies which can all detect tau phosphorylation, and with an anti-pCDK5 antibody that can detect a protein involved in tau phosphorylation. According to the results, ibrutinib was found to significantly reduce tau phosphorylation only in the cortex of 5×FAD mice as measured by immunohistochemical staining with the anti-AT8 antibody (FIGS. 24A-24E); to significantly reduce tau phosphorylation in both the cortex and the hippocampus of 5×FAD mice as measured by immunohistochemical staining with the anti-AT100 antibody (FIGS. 25A-25E); to significantly reduce tau phosphorylation in the cortex of 5×FAD mice and to reduce tau phosphorylation in the hippocampus as measured by immunohistochemical staining with the anti-AT180 antibody (FIGS. 26A-26E); and to significantly reduce CDK phosphorylation in both the cortex and the hippocampus of 5×FAD mice as measured by immunohistochemical staining with an antibody against CDK, which induces tau phosphorylation (FIGS. 27A-27B).

Consequently, ibrutinib was found to have ability to modulate amyloid plaque formation, tau phosphorylation, neuroinflammation prevention, and memory improvement, thereby finding applications as a therapeutic agent for prevention, alleviation, or treatment of degenerative brain disease.

The present disclosure has been described above with reference to the embodiments thereof. It will be understood by those skilled in the art that various modifications may be made to the embodiments without departing from the spirit and scope of the disclosure. The disclosed embodiments should, therefore, be considered in an illustrative rather than a limitative aspect. The scope of the present disclosure is defined by the appended claims rather than by the foregoing description, and all differences within the scope of equivalents thereof should be construed as being included in the present disclosure.

The invention claimed is:

1. A method of preventing or treating a degenerative brain disease in a subject in need thereof comprising:
 administering to the subject a pharmaceutically effective amount of a pharmaceutical composition comprising ibrutinib or a pharmaceutically acceptable salt thereof.

2. The method of claim 1, wherein the subject requires inhibiting microglial or astrocytic activity, thereby suppressing damage of activated microglial cells or activated astrocytes on neuronal cells.

3. The method of claim 2, wherein the microglial or astrocytic activity is induced by lipopolysaccharides.

4. The method of claim 1, wherein the subject requires inhibiting microglial cell migration.

5. The method of claim 4, wherein the microglial cell migration is induced by lipopolysaccharides.

6. The method of claim 1, wherein the subject requires inhibiting amyloid plaque formation or tau protein phosphorylation.

7. The method of claim 1, wherein the subject requires increasing a number of dendritic spines, a number of synaptophysin, and a number of puncta PSD-95 in neuronal cells.

8. The method of claim 7, wherein the subject requires improving long-term memory, and the degenerative brain disease is Alzheimer's disease.

9. The method of claim 1, wherein the degenerative brain disease is selected from Alzheimer's disease, Parkinson's disease, Huntington's disease, multiple sclerosis, multiple neuronal atrophy, epilepsy, encephalopathy, stroke, memory impairment, cognitive dysfunction, or a learning impairment.

10. The method of claim 1, wherein the pharmaceutical composition is administered intraperitoneally, intravenously, intramuscularly, subcutaneously, intradermally, orally, intranasally, intrapulmonarily or intrarectally.

11. The method of claim 1, wherein the pharmaceutical composition is administered at a dose ranging from 0.001 to 100 mg/kg of the subject.

12. A method of inhibiting activity of microglial cells or astrocytes, comprising:
 administering an effective amount of ibrutinib or a pharmaceutically acceptable salt thereof to a subject in need thereof.

13. A method of inhibiting microglial cell migration induced by lipopolysaccharides (LPS), comprising:
 administering an effective amount of ibrutinib or a pharmaceutically acceptable salt thereof to a subject in need thereof.

* * * * *